US006608076B1

(12) United States Patent
Greenwald et al.

(10) Patent No.: US 6,608,076 B1
(45) Date of Patent: Aug. 19, 2003

(54) CAMPTOTHECIN DERIVATIVES AND POLYMERIC CONJUGATES THEREOF

(75) Inventors: Richard B. Greenwald, Somerset, NJ (US); Hong Zhao, Edison, NJ (US)

(73) Assignee: Enzon, Inc., Bridgewater, NJ (US)

( * ) Notice: Subject to any disclaimer, the term of this patent is extended or adjusted under 35 U.S.C. 154(b) by 0 days.

(21) Appl. No.: 10/147,168

(22) Filed: May 16, 2002

(51) Int. Cl.[7] .................. A61K 31/4745; C07D 471/12
(52) U.S. Cl. .................. 514/285; 546/70; 546/47; 514/283
(58) Field of Search .................. 546/70, 47; 514/285, 514/283

(56) References Cited

U.S. PATENT DOCUMENTS

| 4,914,205 A | 4/1990 | Sawada et al. |
| 6,342,506 B1 | 1/2002 | Giovanella et al. |

FOREIGN PATENT DOCUMENTS

EP    1 029 863 A1    8/2000

OTHER PUBLICATIONS

John A. Adamovics and C. Richard Hutchinson Prodrug Analogues of the Antitumor Alkaloid Camptothecin Journal of Medicinal Chemistry, 1979, vol. 22, No. 3, PP310–314.
Hertzberg, et al. Modification of the Hydroxy Lactone Ring of Camptothecin: Inhibition of Mammalian Topoisomerase I and Biological Activity J. Med. Chem. 1989, 32, 715–720.
Yaegashi, et al. Synthesis and Antitumor Activity of 20(S)–Camptothecin Derivatives. A–Ring–Substituted 7–Ethylcamptothecins and Their E–Ring–Modified Water–Soluble Derivatives Chem. Pharm. Bull. 42(12) 2518–2525 (1994) vol. 42, No. 12.

Sawada et al. Chemical Modification of an Antitumor Alkaloid, 20(S)–Camptothecin: E–Lactone Ring–Modified Water–Soluble Derivatives of 7–Ethylcamptothecin Chem. Pharm. Bull. 41(2) 310–313 (1993) vol. 41, No. 2.

*Primary Examiner*—C. S. Aulakh
(74) *Attorney, Agent, or Firm*—Muserlian, Lucas & Mercanti, LLP

(57) ABSTRACT

Polymeric conjugates of camptothecin derivatives having increased circulating half-lives are disclosed. In preferred aspects, the E ring lactone of the camptothecin derivative is opened and functionalized to allow attachment of a polymer such as PEG in the 17- or 20-position thereof. A representative example of such compounds is

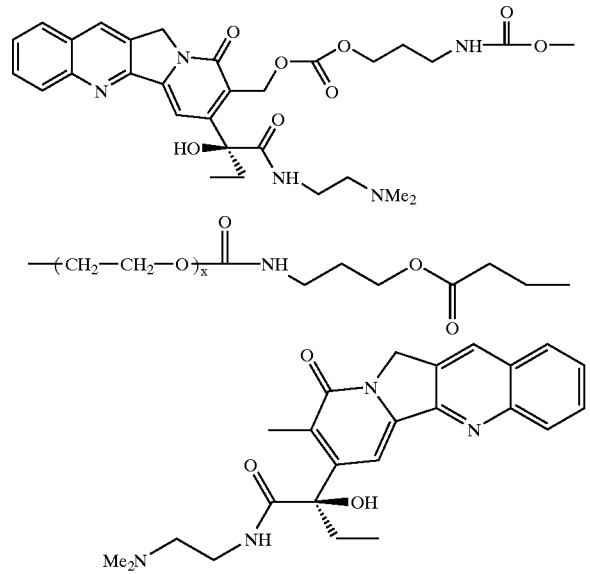

Methods of preparing and using the same are also disclosed.

30 Claims, 6 Drawing Sheets

Scheme 1b.

Scheme 2a.

Scheme 2b.

Scheme 3a.

Scheme 3a.

CAMPTOTHECIN DERIVATIVES AND POLYMERIC CONJUGATES THEREOF

TECHNICAL FIELD

The present invention relates to polymeric derivatives of camptothecin and related topoisomerase inhibitor compounds. More particularly, the invention relates to camptothecin derivatives in which the E ring lactone has been modified to allow attachment of substantially non-antigenic polymers.

BACKGROUND OF THE INVENTION

Camptothecin is a water-insoluble cytotoxic alkaloid produced by *Camptotheca accuminiata* trees indigenous to China and *Nothapodytes foetida* trees indigenous to India. Camptothecin and related analogs are known to be potential anticancer agents and have demonstrated therapeutic activity in vitro and in vivo.

Over the years, various proposals have been made to increase the water solubility and/or therapeutic and pharmacokinetic properties of camptothecin analogs. One early attempt to increase the water solubility of camptothecin is disclosed in U.S. Pat. No. 4,943,579 (hereinafter the '579 patent). The '579 patent discloses certain simple 20(S)-camptothecin amino acid esters in their salt forms as water soluble prodrugs. As evidenced by the data provided in Table 2 of the '579 patent, hydrolysis is rapid. Consequently, at physiologic pH, the insoluble base is rapidly generated after injection, binds to proteins and is quickly eliminated from the body before full therapeutic effect can be achieved. A related effort was directed to developing a water-soluble camptothecin sodium salt. Unfortunately, the water-soluble sodium salt of camptothecin remained too toxic for clinical application (Gottlieb et al,. 1970 *Cancer Chemotlier, Rep.* 54, 461; Moertel et al,. 1972 ibid, 56, 95; Gottlieb et al., 1972 ibid, 56, 103).

Other attempts at improving the solubility of camptothecin analogs are provided by Greenwald et al. For example, commonly-assigned U.S. Pat. No. 5,965,566 discloses camptothecin attached to a bifunctional PEG using an amino acid-based linkers. U.S. Pat. No. 6,011,042 discloses polymeric derivatives of 10-hydroxycamptothecin. The PEG-derivatives provide the artisan with a water soluble prodrug which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations.

The E-lactone ring is thought to be essential for anticancer activity. Nonetheless, Sawada et al. have suggested in U.S. Pat. No. 4,914,205 and Chem. Pharm. Bull. 41(2) 310–313 (1993) prodrugs of camptothecin and the 7-ethyl derivative thereof having a modified E-lactone-ring. Specifically, the E-lactone ring is opened to provide 17-O-acyl derivatives and the authors demonstrated improved solubility of HCl salts thereof when compared to the native alkaloid. In spite of the increases in solubility demonstrated by the open lactone E-ring derivatives, further improvements have been sought. For example, after administration, the prodrug must be converted back into its active form in order to have biological (anticancer) activity. Consequently, these derivatives are highly dependent upon the hydrolysis of the respective hydroxy-acids to free the 17-hydroxyl group in order to regenerate the E-ring lactone. Such conversions, however, are difficult to predict. It would be highly desirable to provide E-lactone ring modified camptothecin analogs with extended circulating half lives and more predictable rates of regenerating the closed lactone ring. The present invention addresses this need.

SUMMARY OF THE INVENTION

In one aspect of the invention, compounds of Formula (I) are provided:

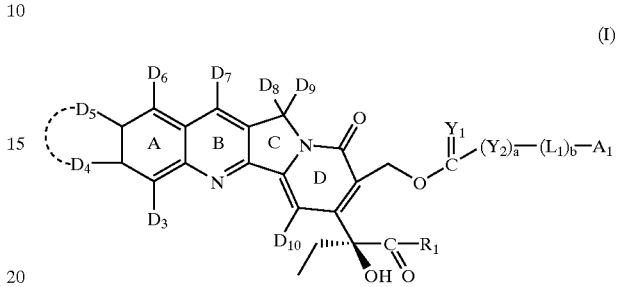

(I)

wherein:
$R_1$ is selected from the group consisting of amino acid residues, peptide residues containing from about 2 to about 10 amino acids, $Y_3$—$(L_2)_p$—$A_2$ and $R_2$;

$Y_3$ is O, S or $NR_3$;

p is zero or one;

$L_2$ is a bifunctional linker;

$Y_1$ is O, S, or $NR_4$;

$Y_2$ is O, S, $CR_5R_6$ or NR7;

$L_1$ is a bifunctional linker;

a and b are independently zero or one;

$A_1$ and $A_2$ are independently selected from the group consisting of hydrogen, amino protecting groups, $NR_8R_9$, amino acid residues, peptide residues containing from about 2 to about 10 amino acids; polymeric residues, $R_{10}$, $SR_{11}$, $NC(O)R_{12}$;

$D_3$–$D_7$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ allkylaryls, $C_{1-8}$ alkoxys, $C_{1-8}$ hydroxy-alkyls, $C_{1-8}$ aminoalkoxy, aryloxys, gycals, $CO_3R_{13}$, $R_{14}$, nitro, cyano, halo, hydroxyl, amino, $SR_{15}$, $NR_{16}R_{17}$ or $OR_{18}$, where $D_4$ and $D_5$ optionally, when taken together, form a saturated 3–7 membered heterocyclic ring which may contain O, S or $NR_{19}$ groups, where $R_{19}$ is hydrogen or a $C_{1-6}$ alkyl;

$D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ allkylaryls and $C_{1-8}$ hydroxy alkyls; and $R_{2-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; except that at least one of $A_1$ and $A_2$ comprise a polymeric residue.

In another aspect of the invention there is provided bifunctional compounds that are formed when at least one of $A_1$ and $A_2$ comprises a polymeric residue and the polymeric residue is functionalized on both the alpha and omega termini to allow two equivalents of the camptothecin to be delivered per equivalent of the polymer which is preferably PEG. Such preferred compositions correspond to formulae (IIIa) and IIIb) below:

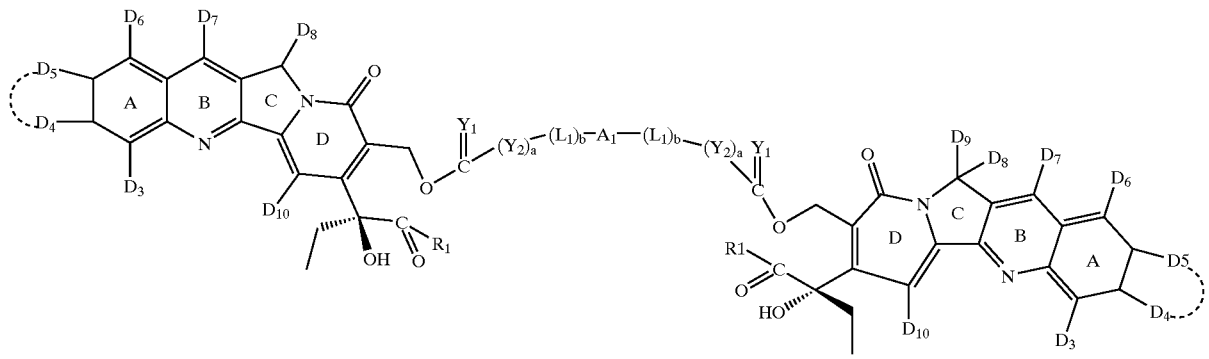

(IIIa)

and

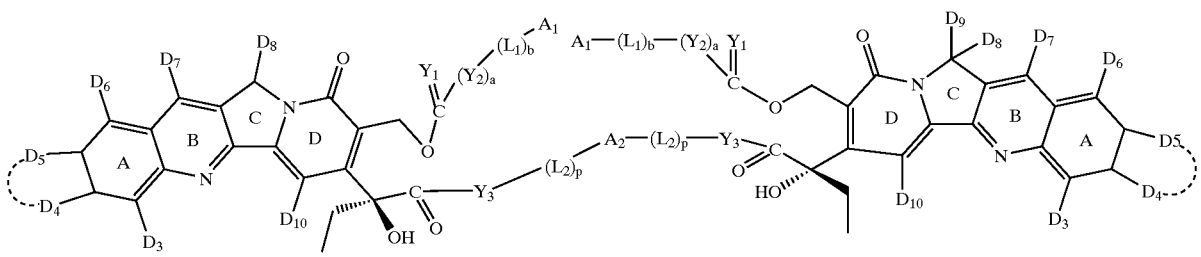

(IIIb)

wherein all variables are as previously defined above.

For purposes of the present invention, the term "residue" shall be understood to mean that portion of a camptothecin derivative or bifunctional spacer which remains after it has undergone a substitution reaction.

Methods of preparing the compositions of the invention and methods of treatment using the same are also provided.

For purposes of the present invention, the term "polymeric residue" or "PEG residue" shall each be understood to mean that portion of the polymer or PEG which remains after it has undergone a reaction with a heteroaromatic amine-containing compound.

For purposes of the present invention, the term "alkyl" shall be understood to include straight, branched, substituted, e.g. halo-, alkoxy-, nitro-, $C_{1-12}$ alkyls, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo- shall be understood to include fluoro, chloro, iodo and bromo.

The term "sufficient amounts" for purposes of the present invention shall mean an amount which achieves a therapeutic effect as such effect is understood by those of ordinary skill in the art.

One advantage of the invention is that the artisan is provided with prodrugs of camptothecin derivatives with improved aqueous solubility.

Another advantage of the compounds of the invention is that in certain preferred embodiments, the releasble polymer not only extends the circulating life of the camptothecin derivative, but it also provides a means for controlling conversion of the open E-ring lactone back to the biologically active form. This result is achieved by virtue of the fact that the open E-ring camptothecin derivative cannot hydrolyze into the closed E lactone ring until the polymer is released.

DETAILED DESCRIPTION OF THE INVENTION

A. Formula (I)

Figure 1:
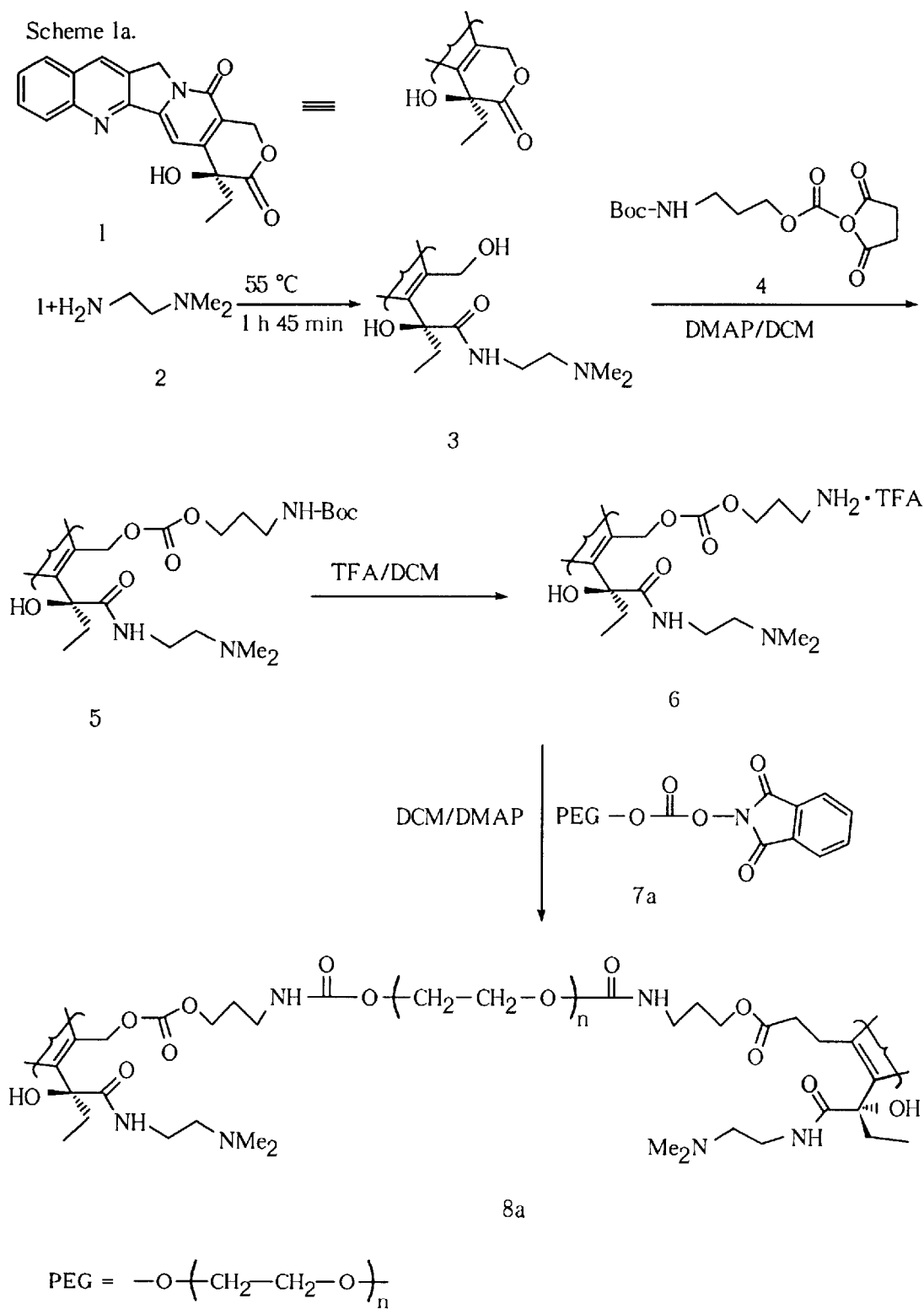
FIGS. 1–6 schematically illustrate methods of forming compounds of the present invention which are described in the Examples.

In one preferred embodiment of the invention, there are provided compounds of the Formula (I):

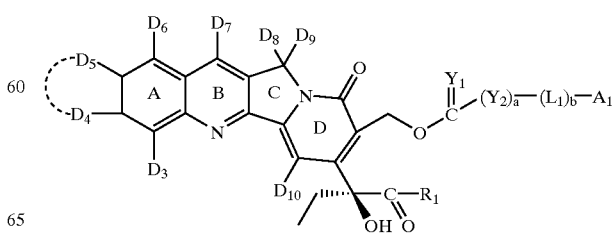

(I)

wherein:

R₁ is selected from the group consisting of amino acid residues, peptide residues containing from about 2 to about 10 amino acids, $Y_3$—$(L_2)_p$—$A_2$ and $R_2$;

$Y_3$ is O, S or $NR_3$;

p is zero or one;

$L_2$ is a bifunctional linker;

$Y_1$ is O, S or NR4;

$Y_2$ is O, S, $CR_5R_6$ or $NR_7$;

$L_1$ is a bifunctional linker;

a and b are independently zero or one;

$A_1$ and $A_2$ are independently selected from the group consisting of hydrogen, amino protecting groups, $NR_8R_9$, amino acid residues, peptide residues containing from about 2 to about 10 amino acids; polymeric residues, $R_{10}$, $SR_{11}$, $NC(O)R_{12}$;

$D_3$–$D_7$ are independently selected from the group consisting of H, $C_{1-8}$ straight or branched alkyls, substituted $C_{1-8}$ straight or branched alkyls, aryls, substituted aryls, arylalkyl, substituted aryalkyls, $C_{1-8}$ alkylaryls, $C_{1-8}$ alkoxys, $C_{1-8}$ hydroxy-alkyls, $C_{1-8}$ aminoalkoxy, aryloxys, gycals, $CO_2R_{13}$, $R_{14}$, nitro, cyano, halo, hydroxyl, amino, $SR_{15}$, $NR_{16}R_{17}$ or $OR_{18}$, where $D_4$ and $D_5$ optionally, when taken together, form a saturated 3–7 membered heterocyclic ring which may contain O, S or $NR_{19}$ groups, where $R_{19}$ is hydrogen or a $C_{1-6}$, alkyl, $D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls and $C_{1-8}$ hydroxyalkyls; and $R_{2-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy; except that at least one of $A_1$ and $A_2$ comprise a polymeric residue.

In many preferred aspects of the invention, one of $A_1$ and $A_2$ includes a polymer residue. The polymer residue optionally includes a capping group designated J herein. Within this aspect of the invention, when $A_1$ is a polymer residue, the capping group J is selected from among, for example, OH, $NH_2$, SH, $CO_2H$, $C_{1-6}$ alkyl moieties and

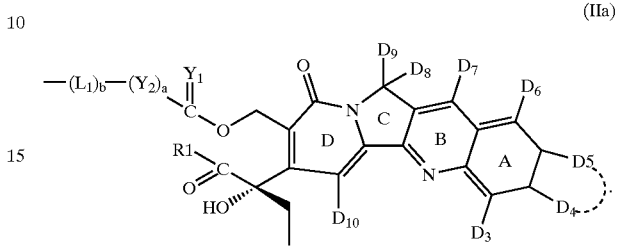

(IIa)

Alternatively, when $R_1$ is $Y_3$—$(L_2)_p$—$A_2$ in formula (I), and $A_2$ is a polymer residue, the capping group J is selected from among, for example, OH, $NH_2$, SH—, $CO_2H$, $C_{1-6}$ alkyl moieties and

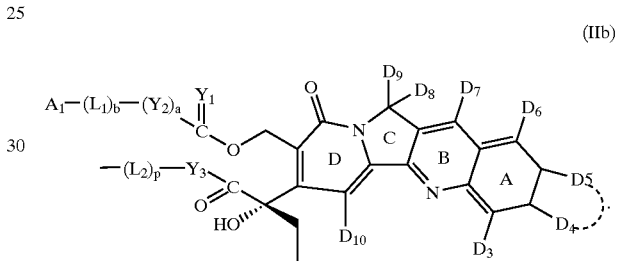

(IIb)

The preferred capping groups allow preferred compositions of (IIIa) and (IIIb), respectively,

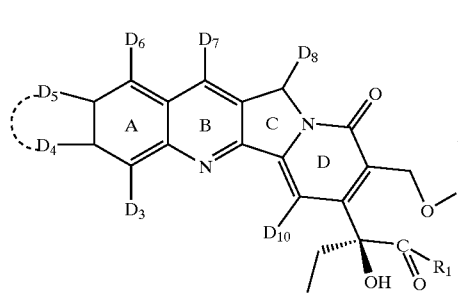

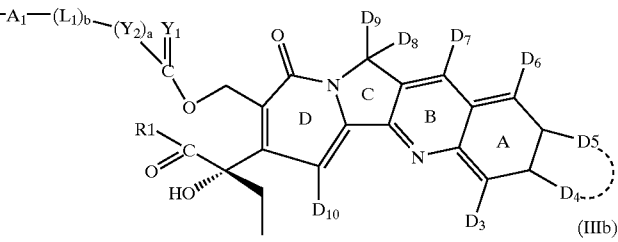

(IIIa)

and

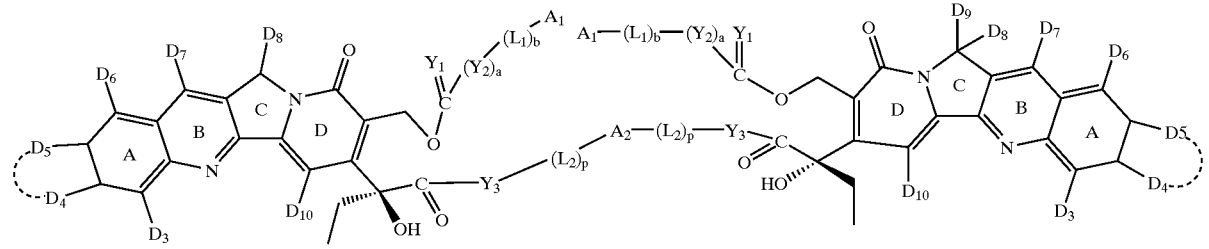

(IIIb)

to be formed, wherein all variables are as previously defined.

When $L_1$ and/or $L_2$ include an amino acid residue, the amino acid can be selected from any of the known naturally-occurring L-amino acids is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. When $L_1$ and/or $L_2$ include a peptide, the peptide ranges in size, for instance, from about 2 to about 10 amino acid residues. In one preferred embodiment, the peptide is Gly-Phe-Leu-. Alternatively, glycine can be added to the aforementioned trippeptide after leucine to form a 4 residue peptide.

The amino acid residues are preferably of the formula

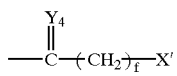

wherein X' is O, S or $NR_{34}$, $Y_4$ is O, S or $NR_{35}$, and f is a positive integer from about 1 to about 10, preferably 1; and $R_{34}$ and $R_{35}$ are independently selected from the same group as that which defines $R_{31}$ but each is preferably H or lower alkyl.

Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-amino-adipic acid, beta-alanine, beta-aminopropionic acid, 2-aminobutyrc acid, 4-amino-butyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2-diaminopimelic acid, 2,3-diaminopropionic acid, n-ethylglycine, N-ethylasparagine, 3-hydroxyproline, 4-hydroxyproline, isodesmo-sine, allo-isoleucine, N-methylglycine, sarcosine, N-methylisoleucine, 6-N-methyl-lysine, N-methylvaline, norvaline, norleucine, ornithine, and others too numerous to mention, that are listed in 63 Fed. Reg., 29620, 29622, incorporated by reference herein.

Short peptides are, for example, peptides ranging from 2 to about 10, or more, amino acid residues, as mentioned supra.

Within most aspects of the invention, the following embodiments are preferred:

$Y_2$ and $Y_2$ are each oxygen, $R_2$–$R_{14}$ and $D_3$–$D_{10}$ are each hydrogen, $L_1$ is selected from among $(CH_2)_n$,
$(CH_2)_3NH$—$C(O)$
$(CH_2)_3NH$—
—$NH(CH_2CH_2O)_n(CH_2)_nNR_{22}$—,
—$NH(CH_2CH_2O)_n$—,
—$NH(C_{23}R_{24})_nO$—,
—$C(O)(CR_{23}R_{24})_nNHC(O)(CR_{25}R_{26})_qNR_{27}$—,
—$C(O)O(CH_2)_nO$—,
—$C(O)(CR_{23}R_{24})_nNR_{27}$—,
—$C(O)NH(CH_2CH_2O)_n(CH_2)_nNR_{27}$—,
—$C(O)O$—$(CH_2CH_2O)_nNR_{27}$—,
—$C(O)NH(CR_{23}R_{24})_nO$—,
—$C(O)O(CR_{23}R_{24})_nO$—,
—$C(O)NH(CH_2CH_2O)_n$—,

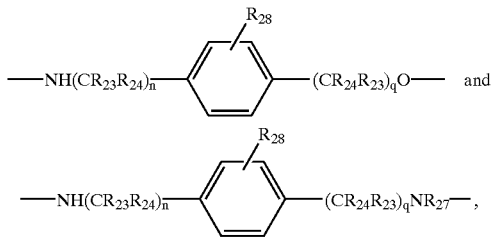

wherein
$R_{22-27}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$R_{28}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and
n and q are independently selected positive integers.

$L_2$ is preferably selected from among:
$(CH_2)_j$
$(CH_2CH_2O)_2(CH_2)_2NH$,
—$NH(CH_2CH_2O)_j(CH_2)_kNR_{29}$—,
—$NH(CH_2CH_2O)_j$—,
—$NH(CR_{30}R_{31})_jO$—,
—$C(O)(CR_{30}R_{31})_jNHC(O)(CR_{32}R_{33})_jNR_{29}$—,
—$C(O)O(CH_2)_kO$—,
—$C(O)(CR_{30}R_{31})_jNR_{29}$—,
—$C(O)NH(CH_2CH_2O)_j(CH_2)_kNR_{29}$—,
—$C(O)O$—$(CH_2CH_2O)_jNR_{29}$—,
—$C(O)NH(CR_{30}R_{31})_jO$—,
—$C(O)O(CR_{30}R_{31})_jO$—,
—$C(O)NH(CH_2CH_2O)_j$—,

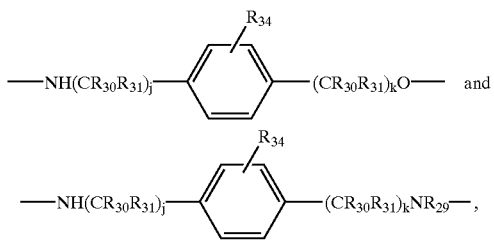

wherein
$R_{29-33}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
$R_{34}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and j and k are independently selected positive integers.

B. Substantially Non-Antigenic Polymers

As stated above, $A_1$ and $A_2$ can comprise polymer residues. The polymer residues are preferably water soluble and substantially non-antigenic. Particularly preferred polymers useful in the compositions of the present invention include polyalkylene oxides such as polyethylene glycol. The polymer residues optionally the previously mentioned capping groups, designated J, which allows a bifunctional or bis-polymer system to be formed.

In those aspects of the invention where $A_1$ includes the polyethylene glycol residue, the PEG derivatives can be selected from the following non-limiting list:

—J—O—$(CH_2CH_2O)_x$—,

J—O—$(CH_2CH_2O)_x$—$CH_2C(O)$—O—,

J—O—$(CH_2CH_2O)_x$—$CH_2CH_2NR_{20}$—,

J—O—$(CH_2CH_2O)_x$—$CH_2CH_2SH$—,

—O—$C(O)CH_2$—O—$(CH_2CH_2O)_x$—$CH_2C(O)$—O—,

—$NR_{20}CH_2CH_2$—O—$(CH_2CH_2O)_x$—$CH_2CH_2NR_{20}$—, and

—$SHCH_2CH_2$—O—$(CH_2CH_2O)_x$—$CH_2CH_2SH$—, wherein:

x is the degree of polymerization;

$R_{20}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy and J is a capping group.

Similarly, in those aspects of the invention where $A_2$ includes the polyethylene glycol residue, the PEG derivatives can be selected from the following non-limiting list:

of J—O—$(CH_2CH_2O)_x$—

J—O—$(CH_2CH_2O)_x$—$CH_2C(O)$—O—,

J—O—$(CH_2CH_2O)_x$—$CH_2CH_2NR_{21}$—,

J—O—$(CH_2CH_2O)_x$—$CH_2CH_2SH$—,

—O—$C(O)CH_2$—O—$(CH_2CH_2O)_x$—$CH_2C(O)$—O—,

—$NR_{21}CH_2CH_2$—O—$(CH_2CH_2O)_x$—$CH_2CH_2NR_{21}$—, and

—$SHCH_2CH_2$—O—$(CH_2CH_2O)_x$—$CH_2CH_2SH$—, wherein:

x is the degree of polymerization;

$R_{21}$ is selected from the group consisting of hydrogen, $C_1$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy and J is a capping group.

For the purpose of the present invention the structure:

—O—$(CH_2CH_2O)_x$— wherein x is a positive integer, is referred to as PEG throughout the application.

The degree of polymerization for the polymer (x) can be from about 10 to about 2,300. This represents the number of repeating units in the polymer chain and is dependent on the molecular weight of the polymer. In certain preferred aspects, the amount of polymerization is preferably sufficient to provide the polymer with a molecular weight of at least about 20,000 daltons. Since the ethylene glycol monomer has a molecular weight of 44, (x) is preferably at least about 454. The (J) moiety is a capping group as defined herein, i.e. a group which is found on the terminal of the polymer and, in some aspects, can be selected from any of $NH_2$, OH, SH—, $CO_2H$, $C_{1-6}$ alkyls or other PEG terminal activating groups, as such groups are understood by those of ordinary skill.

Also useful are polypropylene glycols, branched PEG derivatives such as those described in commonly-assigned U.S. Pat. No. 5,643,575, "star-PEG's" and multi-armed PEG's such as those described in Shearwater Corporation's 2001 catalog "Polyethylene Glycol and Derivatives for Biomedical Application". The disclosure of each of the foregoing is incorporated herein by reference. It will be understood that the water-soluble polymer can be functionalized for attachment to the bifunctional linkage groups if required without undue experimentation.

In many aspects of the present invention, bis-activated polyethylene glycols are preferred when di- or multi-substituted polymer conjugates are desired. Alternatively, polyethylene glycols (PEG's), mono-activated, $C_{1-4}$ alkyl-terminated polyalkylene oxides (PAO's) such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting $CH_3O$-PEG-OH (mPEG-OH) to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in average molecular weight, the polymer portion of the pro-drug is at least about 20,000 Da average in most aspects of the invention. Preferably, the polymer portion of the compositions has a weight average molecular weight of from about 20,000 Da to about 100,000 Da and more preferably from about 25,000 Da to about 60,000 Da. The average molecular weight of the polymer selected for inclusion in the prodrug must be sufficient so as to provide sufficient circulation of the prodrug before hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment, and as an alternative to PAO-based polymers, $A_1$ and $A_2$ can optionally comprise one or more other effectively non-antigenic materials such as dextran, polyvinyl alcohols, carbohydrate-based polymers, hydroxypropylmethacrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bifunctional linking groups are also contemplated.

C. Camptothecin and Camptothecin Analogs

Camptothecin and certain related analogues and derivatives share the structure:

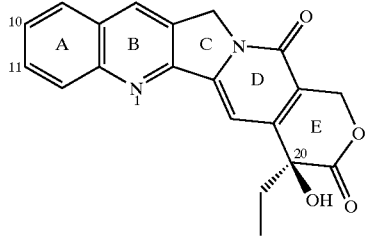

From this core structure, various derivatives are known. For example, the A ring in either or both of the 10- and 11-positions can be substituted with an OH. The A ring can also be substituted in the 9-position with a straight or branched $C_{1-30}$ alkyl or $C_{1-7}$ alkoxy, optionally linked to the ring by a heteroatom i.e. O or S. The B ring can be substituted in the 7-position with a straight or branched $C_{1-30}$ alkyl or substituted alkyl-, $C_{5-8}$ cycloalkyl, $C_{1-30}$ alkoxy, phenyl alkyl, etc., alkyl carbamate, alkyl carbazides, phenyl hydrazine derivatives, amino, aminoalkyl, aralkyl, etc. Other substitutions are possible in the C, D and E rings. See, for example, U.S. Pat. Nos. 5,004,758, 4,943,579, Re 32,518, 4,894,456, 5,225, 5,053,512, 4,981,968, 5,049,668, 5,106, 742, 5,180,722, 5,244,903, 5,227,380, 5,122,606, 5,122,526, and 5,340,817, the contents of each of which are incorporated herein by reference.

In most aspects of the invention, the camptothecin derivatives which are employed in the formation of the compositions of the present invention are generally of the formula

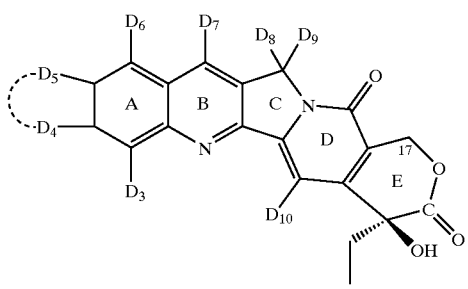

(V)

wherein:

$D_3$–$D_7$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls, $C_{1-8}$ alkoxys, $C_{1-8}$ hydroxy-alkyls, $C_{1-8}$ aminoalkoxy, aryloxys, gycals, $CO_2R_{13}$, $R_{14}$, nitro, cyano, halo, hydroxyl, amino, $SR_{15}$, $NR_{16}R_{17}$ or $OR_{18}$, where $D_4$ and $D_5$ optionally, when taken together, form a saturated 3–7 membered heterocyclic ring which may contain O, S or $NR_{19}$ groups, where $R_{19}$ is hydrogen or a $C_{1-6}$ alkyl;

$D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls and $C_{1-8}$ hydroxyalkyls; and $R_{8-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy.

In other preferred aspects of the invention, the following can be used:

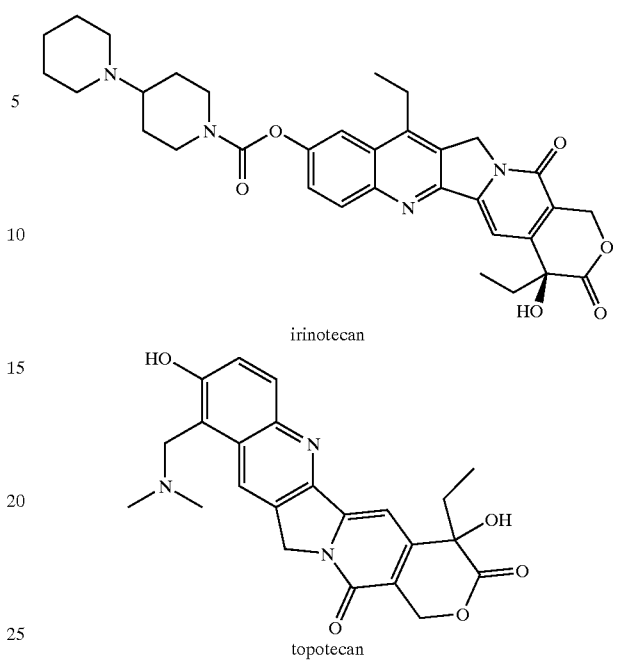

irinotecan topotecan

Still further camptothecin analogs which can be used in the practice of the present invention include, 10,11-oxycamptothecin, 10,11-methylene dioxycamptothecin, 7-ethylcamptothecin, 9-amino-camptothecin, to name but a few.

Those of ordinary skill will realize that the foregoing is merely illustrative of the camptothecin derivatives useful in practicing the present invention. The only limitations on the camptothecin derivatives useful in the invention is that the specific derivative must be capable of undergoing the opening of the E-lactone ring, allowing a polymer to be attached thereto and, after administration, allowing hydrolysis to occur which allows the E-lactone ring to be re-formed in vivo.

D. Synthesis of the Camptothecin-polymeric Prodrugs

Synthesis of specific representative polymer prodrugs is set forth in the Examples. Generally, however, in one preferred method of preparing the prodrug transport systems of the present invention, the E-lactone ring is opened, a capped bifunctional linker is attached at the 17-position of the open lactone ring, the blocking group is removed and followed by PEGylation with appropriate solvent and coupling agent, if required. The lactone ring can be opened using known techniques such as by dissolving the camptothecin derivative in N,N-dimethylethylenediamine (2 in the examples) or in isopropylamine (9 in the examples) or other suitable reagent solvents containing a primary amine and heating the reaction solution for a sufficient amount of time to allow the ring to be opened.

Once the E ring has been opened, the artisan is provided with a camptothecin derivative of the formula:

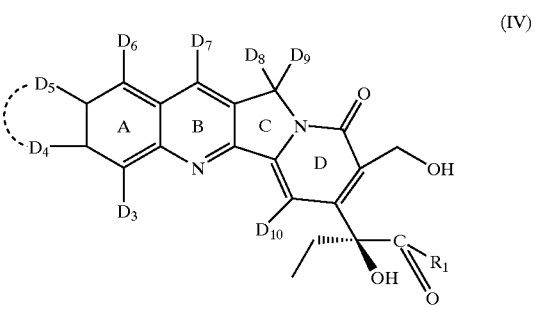

(IV)

wherein:
R₁ is selected from the group consisting of amino acid residues, peptide residues containing from about 2 to about 10 amino acids, $Y_3$—$(L_2)_p$—$A_2$ and $R_2$;
$Y_3$ is O, S or $NR_3$;
p is zero or one;
$L_2$ is a bifunctional linker;
$A_2$ is selected from the group consisting of hydrogen, amino protecting groups, $NR_8R_9$, amino acid residues, peptide residues containing from about 2 to about 10 amino acids; polymeric residues, $R_{10}$, $SCR_{11}$, $NC(O)R_{12}$;
$D_3$–$D_7$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls, $C_{1-8}$ alkoxys, $C_{1-8}$ hydoxy-alkyls, $C_{1-8}$ aminoalkoxy, aryloxys, gycals, $CO_2R_{13}$, $R_{14}$, nitro, cyano, halo, hydroxyl, amino, $SR_{15}$, $NR_{16}R_{17}$ or $OR_{18}$, where $D_4$ and $D_5$ optionally, when taken together, form a saturated 3–7 membered heterocyclic ring which may contain O, S or $NR_{19}$ groups, where $R_{19}$ is hydrogen or a $C_{1-6}$ alkyl;
$D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls and $C_{1-8}$ hydroxyalkyls; and
$R_{2-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
which is then reacted with a blocked bifunctional spacer to form a protected intermediate. This intermediate is then deblocked and reacted with an activated polymer under conditions sufficient to cause a polymeric conjugate to be formed.

A non-limiting list of activated polymers include bis-succinimidyl carbonate activated PEG (SC-PEG), bis-thiazolidine-2-thione activated PEG (T-PEG), N-hydroxyphthalamidyl carbonate activated PEG (BSC-PEG), see commonly assigned U.S. Ser. No. 09/823,296, the disclosure of which is incorporated herein by reference, succinimidyl succinate activated PEG (SS-PEG), imidazole-activated PEG (PGG-IMD), bis-carboxylic acid- PEG (PEG-$CO_2$H) and mono-activated PEG's such as those found in, for example, in the aforementioned 2001 Shearwater Catalog.

Conjugation of the intermediate to the PEG residue can be carried out in the presence of a coupling agent. A non-limiting list of suitable coupling agents include 1,3-diisopropylcarbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably the substituents are reacted in an inert solvent such as tetrahydrofuran (TBF), acetonitrile ($CH_3CN$), methylene chloride (DCM), chloroform ($CHCl_3$), dimethylformamide (DMF) or mixtures thereof. The reaction is preferably conducted in the presence of a base, such as dimethylaminopyridine (DMAP), diisopropyl ethylamine, pyridine, triethylamine, KOH, potassium t-butoxide and NaOH, etc. and at a temperature from 0 ° C. up to about 22° C. (room temperature).

In an alternative embodiment, the compositions of the present invention are prepared by using the blocked bifunctional spacer to open the E-lactone ring in an inert solvent, acylating the 17-position OH group with, for example acetic or butyric anhydride, deblocking the bifunctional spacer and attaching the polymer. Specifically, the reaction involves reacting a compound of the formula

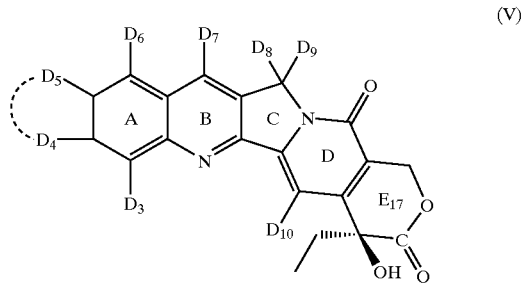

(V)

wherein:
$D_3$–$D_7$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls, $C_{1-8}$ alkoxys, $C_{1-8}$ hydroxy-alkyls, $C_{1-8}$ aminoalkoxy, aryloxys, gycals, $CO_2R_{13}$, $R_{14}$, nitro, cyano, halo, hydroxyl, amino, $SR_{15}$, $NR_{16}R_{17}$ or $OR_{18}$, where $D_4$ and $D_5$ optionally, when taken together, form a saturated 3–7 membered heterocyclic ring which may contain O, S or $NR_{19}$ groups, where $R_{19}$ is hydrogen or $C_{1-6}$ alkyl;
$D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls and $C_{1-8}$ hydroxyalkyls; and
$R_{8-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
with a blocked bifunctional spacer in an inert solvent under conditions sufficient to open the E lactone and form a blocked intermediate of formula (VI)

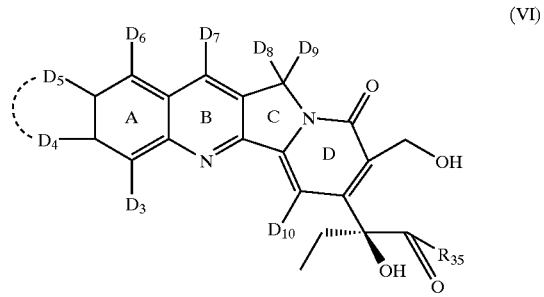

(VI)

wherein $R_{35}$ is a residue of a blocked bifunctional spacer;
b) acylating the $C_{17}$ hydroxyl of the blocked intermediate, and
c) deprotecting the blocked intermediate and reacting it with an activated polymer under conditions sufficient to cause a polymeric conjugate to be formed.

Regardless of the synthesis selected, some of the preferred compounds which result from the synthetic techniques described herein include:

(IIIa)
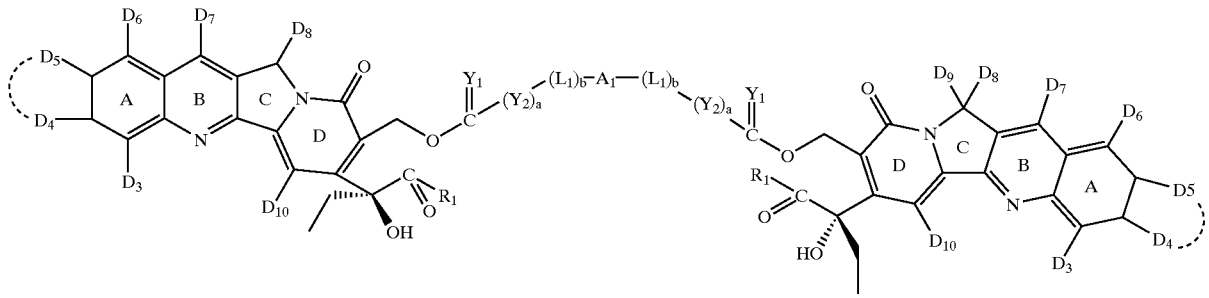
and
(IIIb)
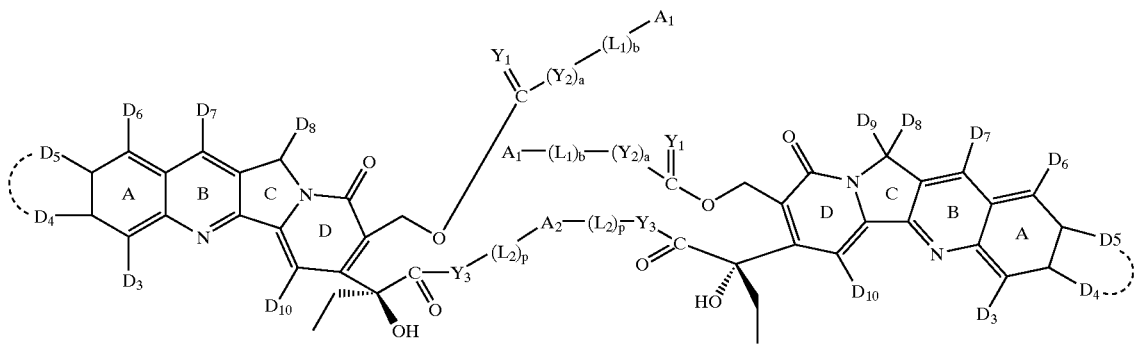
where all variables are as previously defined and
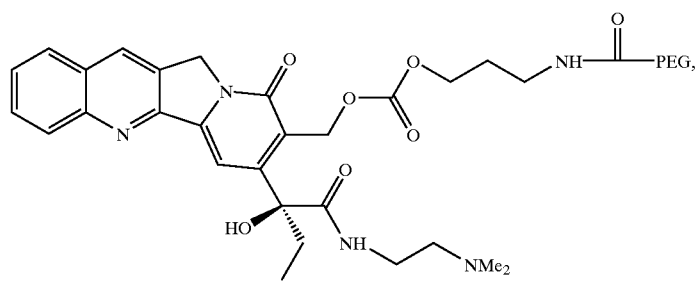
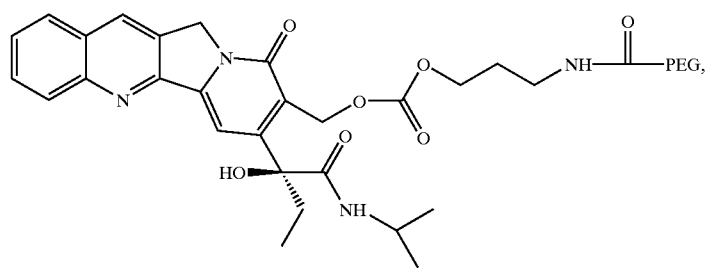

-continued

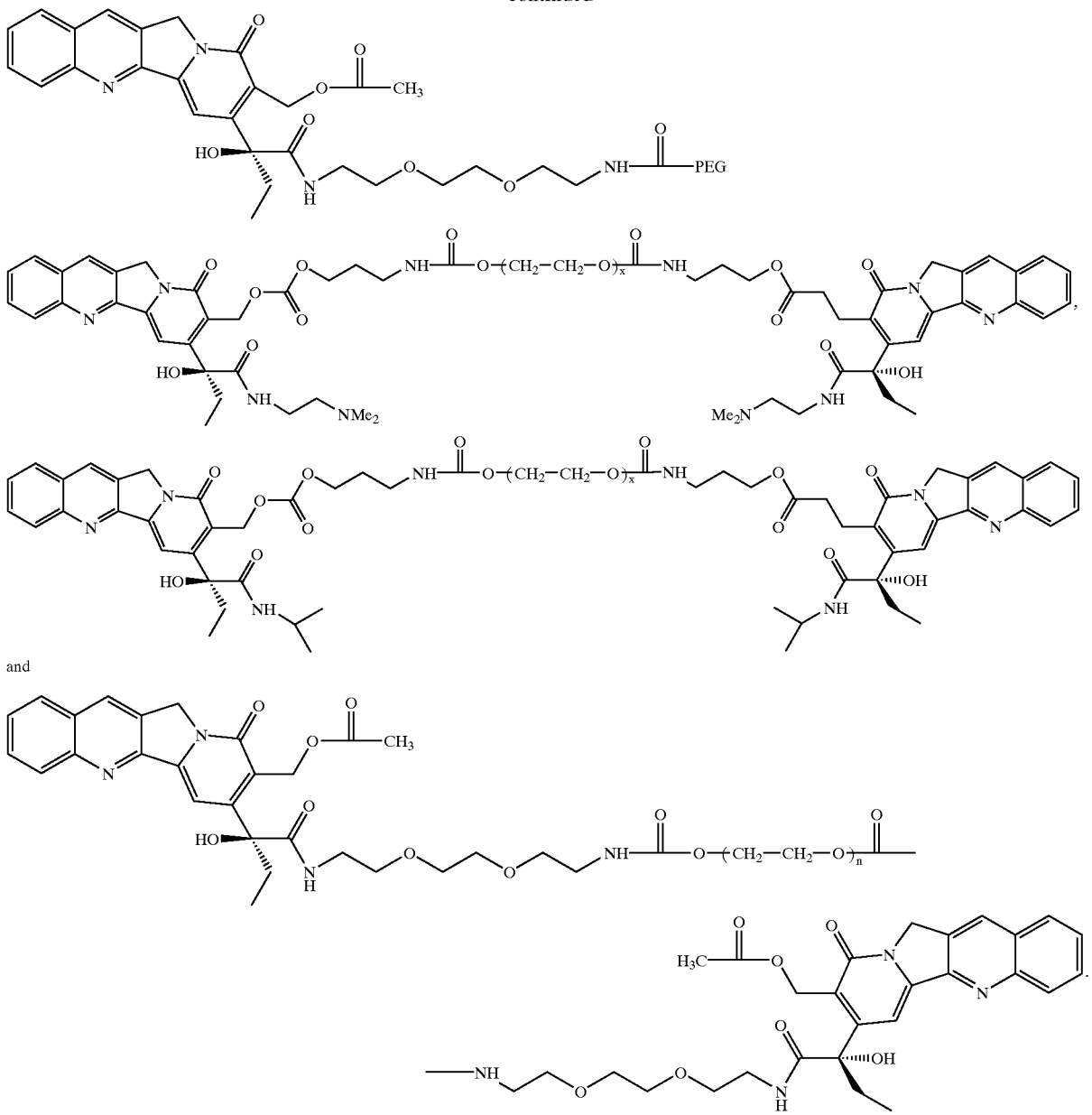

where $PEG=Me-O-(CH_2CH_2O)_x-$ or $-O-(CH_2CH_2O)_x-$

E. Methods of Treatment

Another aspect of the present invention provides methods of treatment for various medical conditions, including topoisomerase inhibitor-related diseases in mammals. The methods include administering to the mammal in need of such treatment, an effective amount of a prodrug, of a camptothecin, camptothecin derivative, camptothecin analog and/or a mixture thereof, such as,those described herein. The compositions are useful for, among other things, treating neoplastic disease, reducing tumor burden, preventing metastasis of neoplasms and preventing recurrences of tumor/neoplastic growths in mammals.

The amount of the inventive composition administered will depend upon several factors, including potency of the parent molecule included therein and specific disease being treated. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis of the open E ring, the molecular weight of the polymer used, if any, etc. In general, dosing is based upon the amount of native (unmodified E-lactone ring) camptothecin or derivative thereof. The camptothecin and derivatives of camptothecin are generally administered in amounts ranging from about 5 to about 500 mg/m$^2$ per day. The range set forth above is illustrative and those skilled in the art will determine the optimal dosing of the prodrug selected based on clinical experience and the treatment indication.

The compositions, including prodrugs, of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral, inhalation and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like. Such administration may also be by infusion into a body space or cavity, as well as by inhalation and/or intranasal routes. In preferred aspects of the invention, however, the prodrugs are parenterally administered to mammals in need thereof.

EXAMPLES

Figure 2:
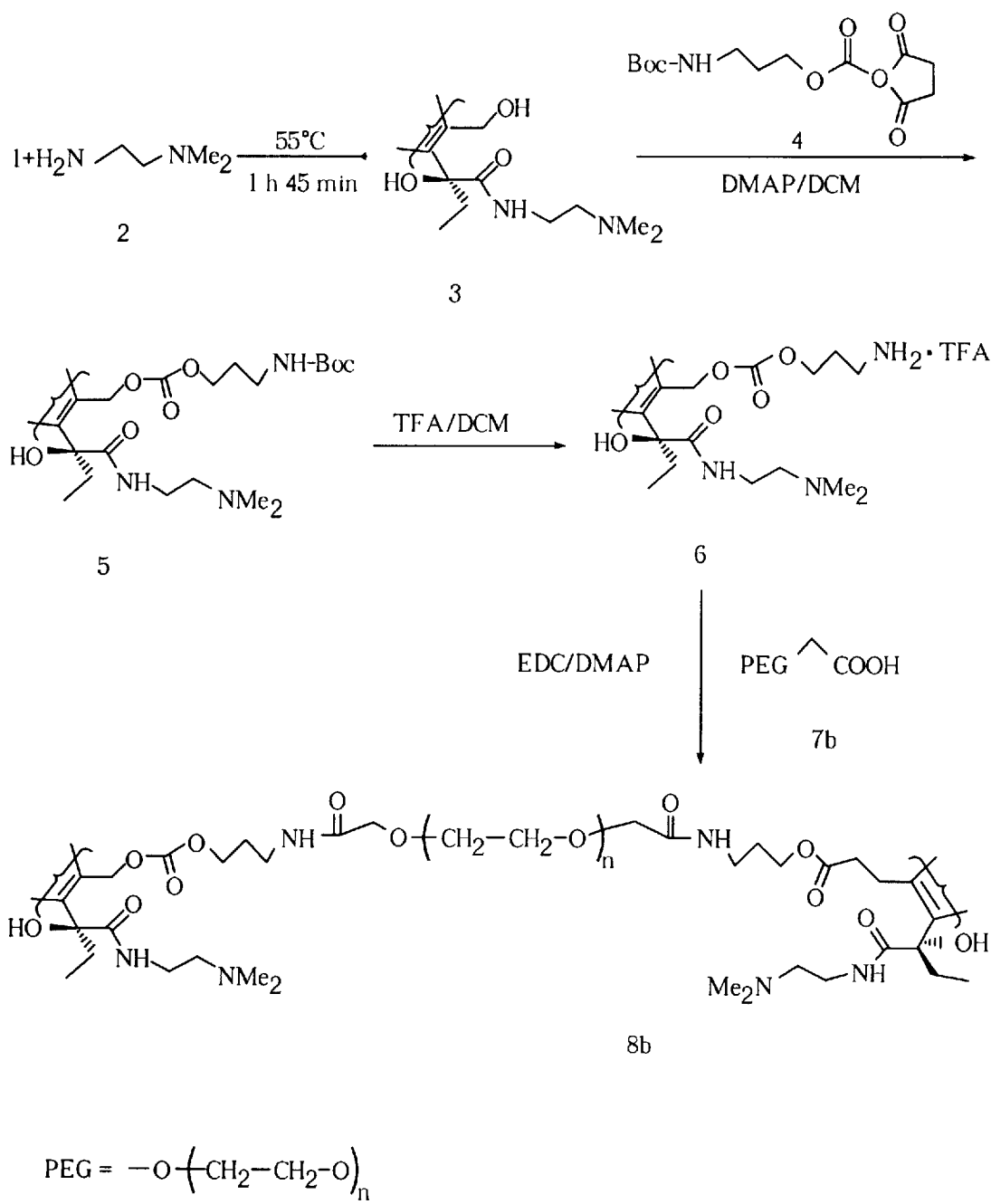
Figure 3:
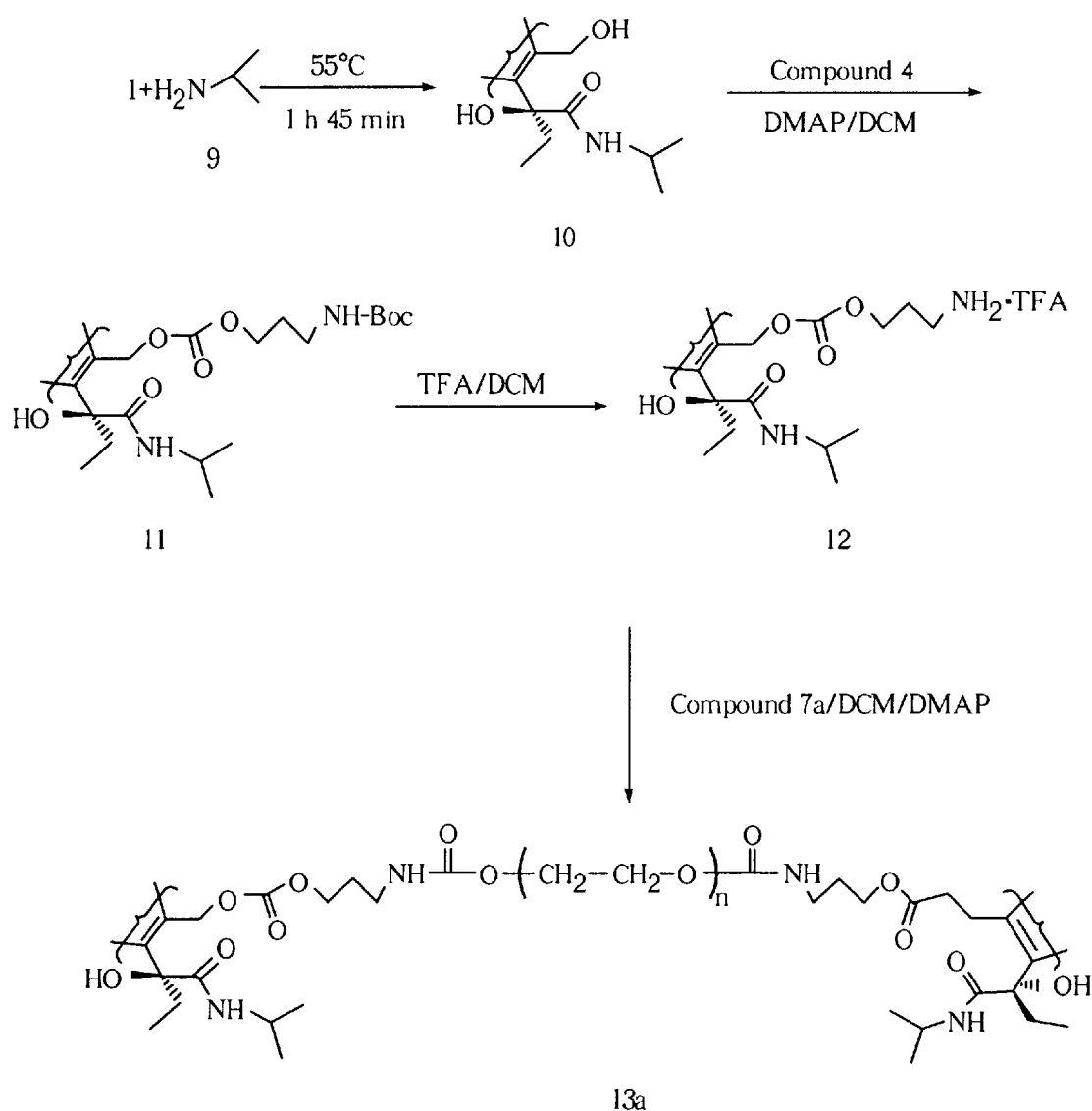
Figure 4:
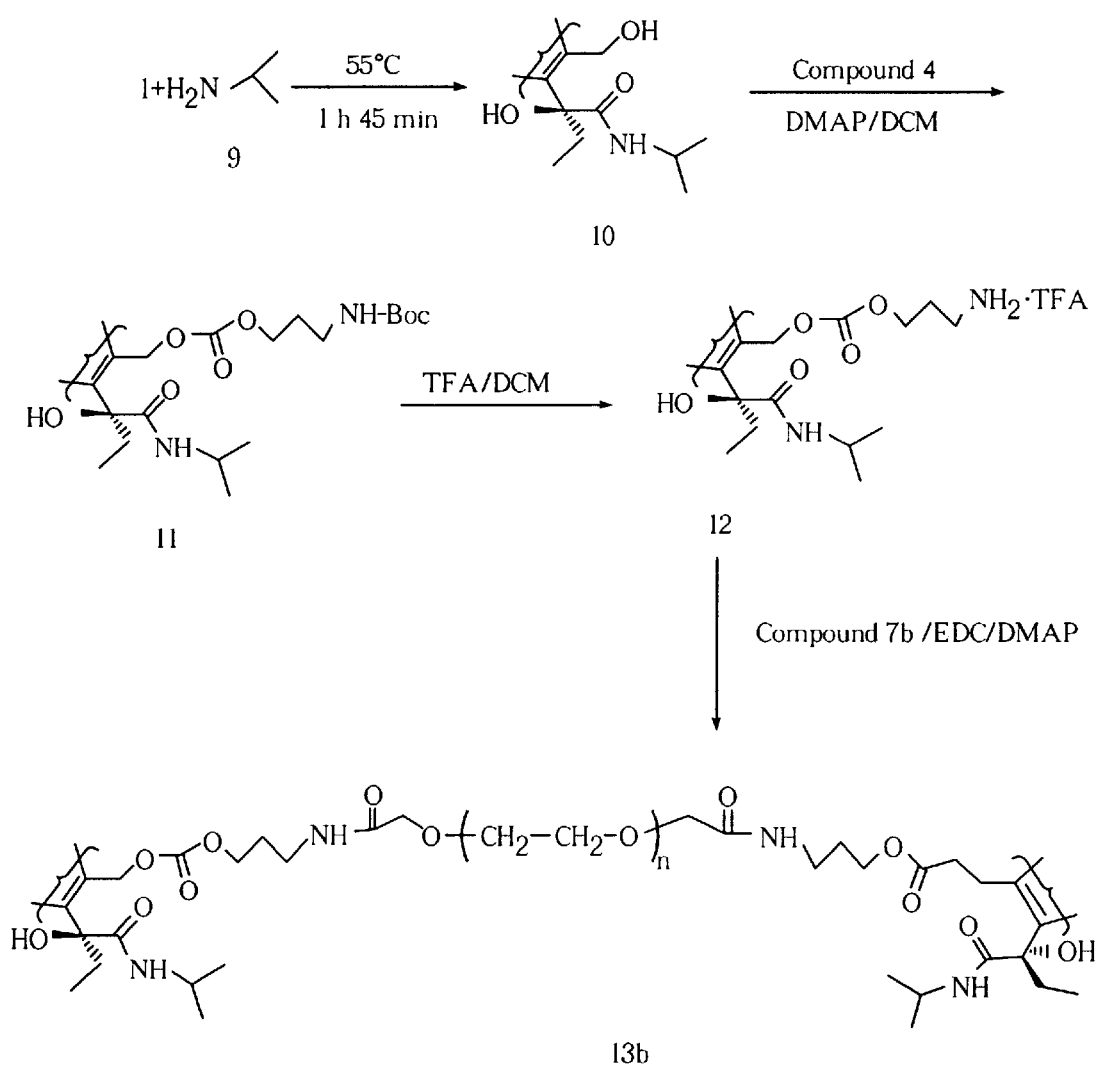
Figure 5:
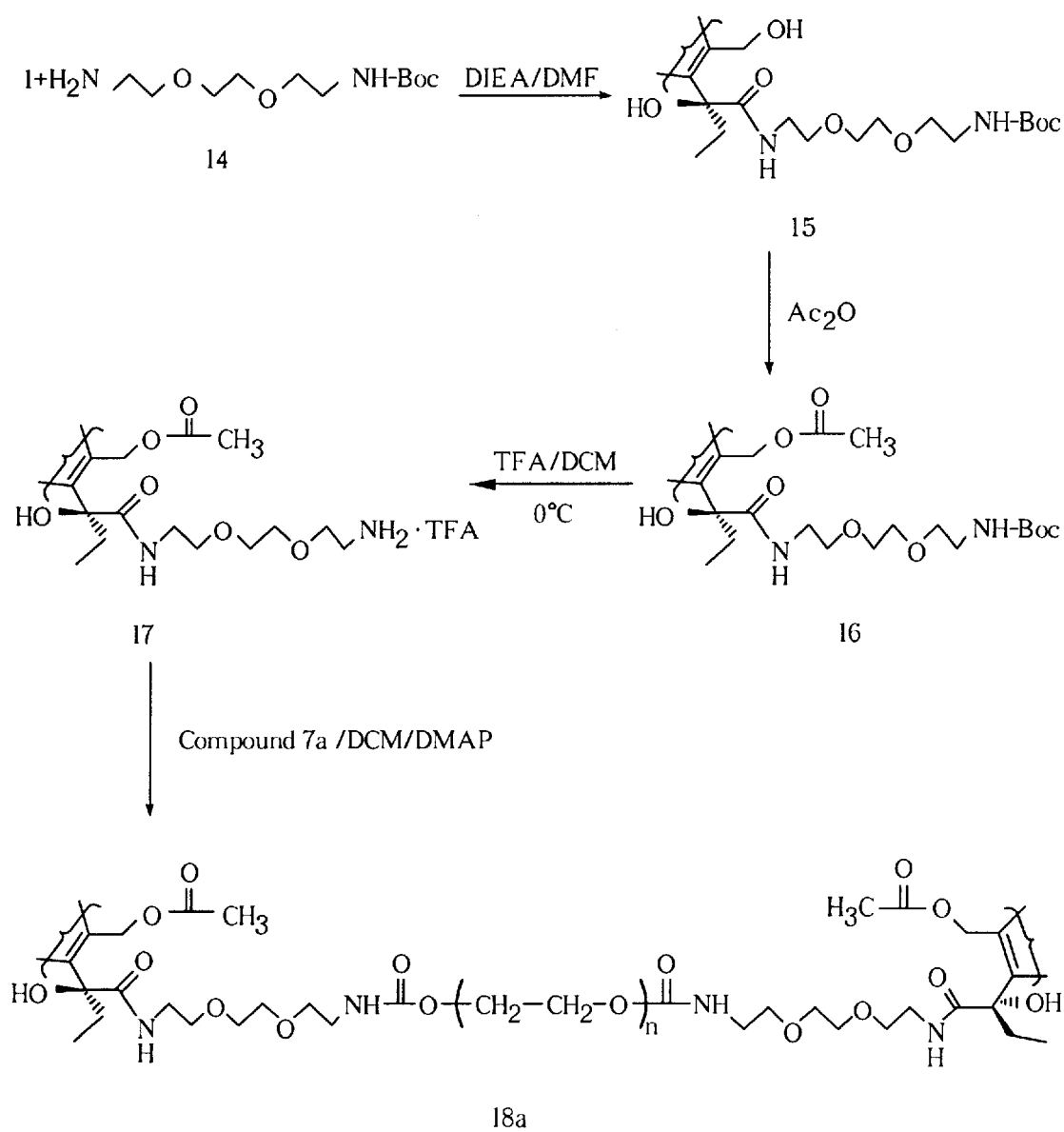
Figure 6:
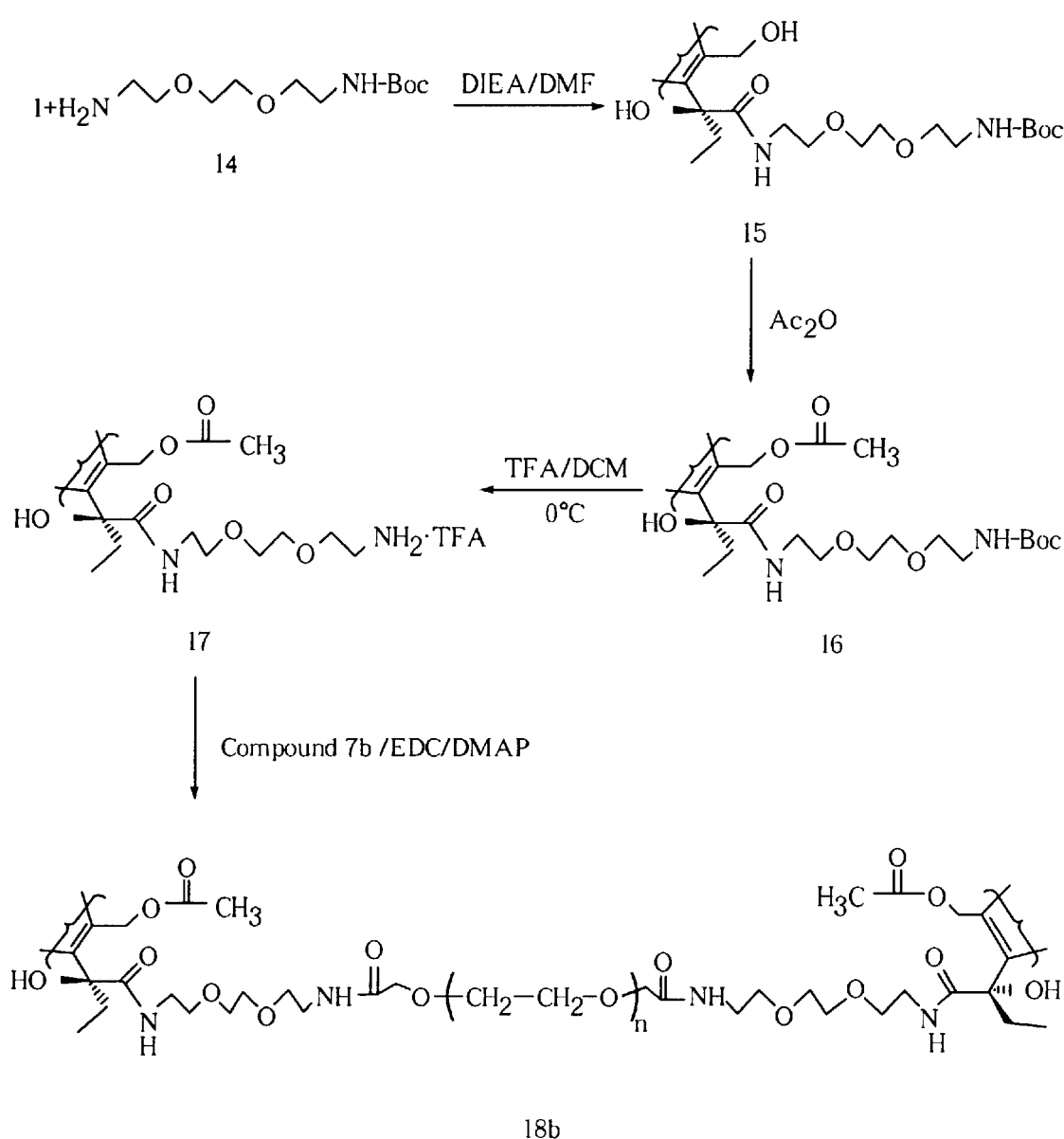

The following examples serve to provide further appreciation of the invention but are not meant in any way to restrict the effective scope of the invention. All compounds mentioned in the following examples are numbered with reference to FIGS. 1–6.

General Procedures. All reactions were run under an atmosphere of dry nitrogen or argon. Commercial reagents were used without further purification. All PEG compounds were 40 kDa and were dried under vacuum or by azeotropic distillation from toluene prior to use. $^{13}$C NMR spectra were obtained at 75.46 MHz using a Varian Mercurye® 300 NMR spectrometer and deuterated chloroform as the solvent unless otherwise specified. Chemical shifts ($\delta$) are reported in parts per million (ppm) downfield from tetramethylsilane (TMS). All PEG conjugated compounds were dissolved in saline for injection prior to in vivo drug treatments and were given as their camptothecin equivalents (absolute amount of camptothecin given). HPLC method. The reaction mixtures and the purity of intermediates and final products were monitored by a Beckman Coulter System Gold® HPLC instrument employing a ZOBAXO® 300 SB C-8 reversed phase column (150×4.6 mm) or a Phenomenex Jupiter® 300A C18 reversed phase column (150×4.6 mm) with a multiwavelength UV detector, using a gradient of 30–90% of acetonitrile in 0.5% trifluoroacetic acid (TFA) at a flow rate of 1 mL/min.

Example 1

Compound 5. Camptothecin (1) (1.44 g, 4.14 mmol) was dissolved in N,N-dimethylethylenediamine (2) (15 mL) and the reaction solution was heated at 50 °C. for 2 hours. The solvent was removed under reduced pressure and the resulting solid washed with ether to give 3, which was suspended with dimethylaminopyridine (DMAP, 1.0 g, 8.88 mmol) and 4 (1.3 g, 4.44 mmol) in anhydrous methylene chloride (DCM, 10 mL). The resulting reaction mixture was refluxed for 4 hours and then stirred at room temperature for 12 hours, washed with 0.1N HCl, dried with MgSO$_4$, filtered, and solvent evaporated under reduced pressure. The crude material was purified on silica gel column to give 5 (0.080 g, 0.13 mmol, 3%). $^{13}$C NMR (67.8 MHz, CDCl$_3$) $\delta$ 167.26, 157.15, 155.77, 153.69, 152.18, 148.76, 146.33, 145.71, 131.14, 130.65, 129.56, 128.37, 128.10, 128.02, 120.10, 95.82, 79.14, 77.83, 77.20, 67.01, 66.50, 50.03, 36.97, 31.84, 29.01, 28.37, 25.59, 7.73.

Example 2

Compound 6. To a solution of 5 (0.080 g, 0.13 mmol) in DCM (1 mL) cooled in an ice bath, trifluoroacetic acid (TFA, 1 mL) was added drop-wise and stirred for 20 min. The solvents were then removed under reduced pressure to give 6 (0.080 g, 0.13 mmol, ~100%). $^{13}$C NMR (67.8 MHz, CDCl$_3$) $\delta$ 167.50, 157.01, 153.95, 146.42, 145.31, 143.81, 134.69, 132.80, 129.26, 129.08, 128.52, 126.56, 120.92, 98.92, 78.27, 77.21, 66.69, 65.27, 50.47, 37.15, 31.33, 26.55, 25.58, 7.53.

Example 3a

Compound 8a. A solution of 6 (0.080 g, 0.13 mmol), 7a (1.50 g, 0.037 mmol), and DMAP (0.031 g, 0.25 mmol) in DCM (8 mL) was stirred at room temperature for 12 hours. The reaction mixture was washed with 0.1NHCl (2×10 mL) and the organic layer evaporated under reduced pressure. The solid residue was crystallized from isopropyl alcohol (IPA, 30 mL) to yield 8a (1.2 g, 0.029 mmol, 79%). $^{13}$C NMR (67.8 MHz, CDCl$_3$) $\delta$ 166.41, 156.36, 155.64, 152.92, 151.50, 148.01, 145.76, 144.89, 130.76, 129.90, 128.84, 127.95, 127.58, 127.29, 119.31, 94.90, 67.0–73.5 (PEG), 66.29, 65.78, 63.05, 49.46, 36.69, 31.12, 28.39, 7.14.

Example 3b

Compound 8b. The procedure of Example 3a is followed, except that PEG-CO$_2$H 7b (1.5 g, 0.037 mmol) and 2 equivalents of EDC is used in place of 7a to form an amide-linked PEG conjugate.

Example 4

Compound 11. 1 (1.44 g, 4.14 mmol) was dissolved in isopropylamine 9 (35 ml) and the solution refluxed for 1.5 hours. The solvent was removed under reduced pressure and the resulting solid washed with ether to give 10, which was suspended with DMAP (0.29 g, 2.36 mmol) and 4 (0.36 g, 1.18 mmol) in anhydrous chloroform (2 mL). The resulting reaction mixture was heated at 60° C. for 1 hour, washed with 0.1N HCl, dried (MgSO$_4$), filtered, and the solvent evaporated under reduced pressure. The crude material was purified by column chromatography to give 11 (0.068 g, 0.11 mmol, 3%). $^{13}$C NMR (67.8 MHz, CDCl$_3$) $\delta$ 171.26, 161.43, 156.41, 155.92, 155.33, 152.09, 148.46, 144.57, 130.66, 130.22, 129.37, 128.37, 127.90, 127.71, 123.90, 100.57, 79.17, 77.20, 75.92, 65.22, 62.13, 50.27, 41.72, 37.09, 32.87, 29.33, 28.46, 22.74, 22.44, 7.90.

Example 5

Compound 12. To a solution of compound 11 (0.68 g, 0.11 mmol) in DCM (1 mL), cooled in an ice bath, was added TFA (1 mL) drop-wise and the solution stirred for 2 hours. The solvents were removed under reduced pressure to give 12 (0.067 g, 0.11 mmol, ~100%). $^{13}$C NMR (67.8 MHz, CDCl$_3$/CD$_3$OD) $\delta$ 171.74, 161.75, 157.19, 154.76, 152.01, 148.27, 144.55, 131.41, 130.62, 128.90, 128.58, 128.08, 127.91, 123.53, 101.24, 78.50, 64.99, 62.33, 50.23, 41.55, 37.06, 32.19, 26.35, 22.32, 22.00, 7.55.

Example 6a

Compound 13a. A solution of 12 (0.067 g, 0.11 mmol), 7a, (1.30 g, 0.032 mmol), and DMAP (0.027 g, 0.22 mmol) in DCM (8 mL) was stirred at room temperature for 12 hours. The reaction mixture was washed with 0.1N HCl (2×10 mL) and the organic layer evaporated under reduced pressure. The solid residue was crystallized from IPA (30 mL) to yield 13a (1.1 g, 0.028 mmol, 86%). $^{13}$C NMR (67.8 MHz, CDCl$_3$) $\delta$ 170.64, 160.74, 155.82, 154.54, 151.65, 147.90, 144.02, 134.37, 130.35, 129.57, 128.77, 128.03, 127.43, 127.20, 99.61, 67.0–73.5 (PEG), 64.63, 63.23, 61.49, 49.71, 41.07, 37.02, 32.11, 28.74, 22.20, 21.84, 7.41.

Example 6b

Compound 13b. The procedure of Example 6a is followed, except that PEG-CO$_2$H 7b (1.5 g, 0.037 mmol) is used with 2 equivalents of EDC in place of 7a to form an amide-linked PEG conjugate.

Example 7

Compound 16. A mixture of 1 (0.34 g, 0.97 mmol), 14 (4.7 g, 19 mmol), and diisopropylethylamine (DIEA, 3.3 mL, 1.4 mmol) in dimethylformamide (DMF, 7 mL) was heated at 70° C. for 48 hours and a clear solution was obtained. The solvent was removed under reduced pressure, and the resulting solid washed with hexane and then ether to give 15 which was suspended in anhydrous DCM (10 mL) and cooled to 0° C. in an ice bath. Acetic anhydride (0.10 mL, 1.1 mmol) and DMAP (0.057 g, 0.47 mmol) were added to the above suspension and stirred for 3 hours at ambient temperature. The reaction mixture was washed with 0.1 N sodium bicarbonate (10 mL), and the organic layer evaporated under reduced pressure. The residue was purified on silica gel column to give pure 16 (0.25 g, 0.39 mmol, 40%). $^{13}$C NMR (67.8 MHz, CDCl$_3$) δ 172.19, 170.95, 161.38, 156.80, 155.91, 151.42, 148.04, 144.05, 130.42, 130.00, 128.92, 127.89, 127.68, 127.58, 127.26, 124.77, 100.60, 79.15, 78.55, 70.14, 69.37, 58.78, 50.23, 40.33, 39.04, 32.93, 28.40, 20.99, 7.92.

Example 8

Compound 17. To a solution of 16 (0.12 g, 0.19 mmol) in DCM (1 mL) cooled in an ice bath was added TFA (1 mL) dropwise and stirred for 30 minutes. Solvent was removed under reduced pressure to give 6(0.12 g, 0.19 mmol, ~100%). $^{13}$C NMR (67.8 MHz, CDCl$_3$) δ 173.01, 172.22, 161.33, 157.08, 149.97, 146.13, 142.92, 132.94, 131.47, 128.55, 128.40, 128.10, 127.67, 127.23, 125.13, 117.41, 113.59, 102.62, 78.65, 70.19, 69.37, 66.48, 58.63, 50.67, 40.06, 39.28, 32.68, 20.78, 7.62.

Example 9a

Compound 18a. A solution of 17 (0.050 g, 0.090 mmol), 7a (1.20 g, 0.030 mmol), and DMAP (0.022 g, 0.18 mmol) in DCM (6 mL) was stirred at room temperature for 12 hours. The reaction mixture was washed with 0.1N HCl (2×10 mL) and the organic layer evaporated under reduced pressure. The solid residue was crystallized from IPA (30 mL) to yield 18a (1.1 g, 0.027 mmol, 89%). $^{13}$C NMR (67.8 MHz, CDCl$_3$) δ 171.82, 170.32, 160.71, 155.75, 155.23, 151.59, 147.82, 143.79, 134.41, 130.30, 129.55, 128.70, 127.90, 127.42, 127.11, 124.07, 99.59, 67.0–73.5 (PEG), 63.14, 58.50, 49.61, 40.17, 38.58, 32.14, 20.48, 7.38.

Example 9b

Compound 18b. The procedure of Example 9a is followed, except that PEG-CO$_2$H 7b (1.5 g, 0.037 mmol) is used with 2 equivalents of EDC in place of 7a to form an amide-linked PEG conjugate.

Example 10

The efficacy of open-form camptothecin analogs against a subcutaneous human mammary carcinoma (MX-1) grown in nude mice was determined as follows. Following at least one week of acclimation, tumors were established by implanting small tumor fragments from donor mice into a single subcutaneous site, on the left axillary flank region of nude mice. The tumor implantation site was observed twice weekly and measured once palpable. The tumor volume for each mouse was determined by measuring two dimensions with calipers and calculated using the formula: tumor volume=(length× width$^2$). When tumors reached the average volume of approximately 75 mm$^3$, the mice were divided into their experimental groups, which consists of untreated controls, PEG$_{40,000}$-ala-20(S)-Camptothecin, compound 8, and compound 18.

The mice were sorted to evenly distribute tumor size, grouped into 4 to 5 mice/cage, and ear punched for permanent identification. Drugs were dosed intravenously via the tail vein as a single dose (Qd1). Mouse weight and tumor sizes were measured at the beginning of study and twice weekly through week 5. The overall growth of tumors was calculated as the mean tumor volume at one week following the end of the treatment. A percent treatment over control (T/C) value was also calculated when the control group's median tumor size reached approximately 800–1100 mm$^3$ and again at one week following treatment. The T/C value in percent is a non-quantitative indication of anti-tumor effectiveness.

Treatments with PEG$_{40,000}$-ala-20(S)-Camptothecin, compounds 8 and 18 all caused significantly (P<0.05) smaller tumor volumes as compared to control mice. In addition, at equivalent doses, there was no significant (P<0.05) difference in the antitumor activity of these three compounds.

TABLE 2

Efficacy Summary of PEG-Camptothecin Against a Human Mammary Carcinoma (MX-1) Xenograft in Nude Mice$^\alpha$

| Compound | Treatment Schedule (mg/kg/dose) | Tumor Volume (mean ± sem) Day 21 | T/C (%)$^\beta$ At 1000 mm$^3$ | Tumor Regression at Day 25 (#/grp) |
|---|---|---|---|---|
| Control | 0 | 2722 ± 223 | — | 0/5 |
| PEG$_{40,000}$-ala-20(S)-Campto. | Qd1 (24) | 15 ± 5 | 1.4 | 5/5 |
| 8 | Qd1 (24) | 21 ± 6 | 3.0 | 5/5 |
| 18 | Qd1 (24) | 14 ± 2 | 2.5 | 4/4 |

$^\alpha$Intravenous treatment in nude mice bearing established tumors (~75 mm$^3$). N = 4 to 5/group.
$^\beta$The median tumor volume of treatment and control groups were measured and compared when the control group's median tumor volume reached approximately 1000 mm$^3$ and one week after final dosage (Day 15). T/C < 42% at 1000 mm$^3$ is considered significant anti-tumor activity by the Drug Evaluation Branch of the NCI.

While applicants are not bound by theory, it is believed that significant conversion of the open lactone E ring into the closed lactone ring has occurred in order to achieve the observed tumor regression.

The various publications, patents, patent applications and published applications mentioned in this application are hereby incorporated by reference herein in their entireties.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:
1. A compound comprising Formula I:

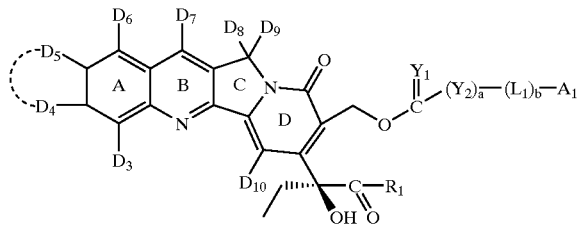

(I)

wherein:
R$_1$ is selected from the group consisting of amino acid residues, peptide residues containing from about 2 to about 10 amino acids, Y$_3$—(L$_2$)$_p$—A$_2$ and R$_2$;
Y$_3$ is O, S or N$_3$;
p is zero or one;
L$_2$ is a bifunctional linker;
Y$_1$ is O, S or NR$_7$;
Y$_2$ is O, S, CR$_5$R$_6$ or NR$_7$;
L$_1$ is a bifunctional linker;
a and b are independently zero or one;
A$_1$ and A$_2$ are independently selected from the group consisting of hydrogen, amino protecting groups, NR$_8$R$_9$, amino acid residues, peptide residues containing from about 2 to about 10 amino acids; polymeric residues, R$_{10}$, SR$_{11}$, NC(O)R$_{12}$;

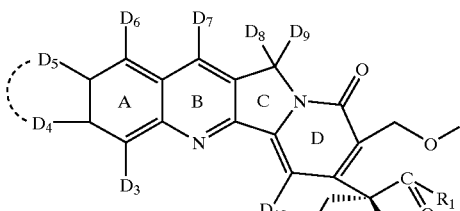

D$_3$–D$_7$ are independently selected from the group consisting of H, C$_{1-8}$ straight or branched alkyls, substituted C$_{1-8}$ straight or branched alkyls, aryls, substituted aryls, arylalkyls, substituted aryalkyls, C$_{1-8}$ alkylaryls, C$_{1-8}$ alkoxys, C$_{1-8}$ hydroxy-alkyls, C$_{1-8}$ aminoalkoxy, aryloxys, gyrals, CO$_2$R$_{13}$, R$_{14}$, nitro, cyano, halo, hydroxyl, amino, SR$_{15}$, NR$_{16}$SR$_{17}$ or OR$_{18}$, where D$_4$ and D$_5$ optionally, when taken together, form a saturated 3–7 membered heterocyclic ring which may contain O, S or NR$_{19}$ groups, where R$_{19}$ is hydrogen or a C$_{1-6}$ alkyl;
D$_8$–D$_9$ are independently selected from the group consisting of H, C$_{1-8}$ straight or branched alkyls, substituted C$_{1-8}$ straight or branched alkyls, aryls, substituted aryls, arylalkyls, substituted aryalkyls, C$_{1-8}$ alkylaryls and C$_{1-8}$ hydroxyalkyls; D$_{10}$ is H, and
R$_{2-18}$ are independently selected from the group consisting of hydrogen, C$_{1-6}$ alkyls, C$_{3-19}$ branched alkyls, C$_{3-8}$ cycloalkyls, C$_{1-6}$ substituted alkyls, C$_{3-8}$ substituted cyloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy, provided that at least one of A$_1$ and A$_2$ comprise a polymeric residue.

2. The compound of claim 1, wherein Y$_1$ and Y$_2$ are each O.

3. The compound of claim 1, wherein R$_2$–R$_{14}$ and D$_3$–D$_9$ are each hydrogen.

4. The compound of claim 1, wherein A$_1$ is a polymer residue.

5. The compound of claim 4, wherein said polymer residue further includes a capping group J, selected from the group consisting of OH, NH$_2$, SH, CO$_2$H, C$_{1-6}$ alkyl moieties and

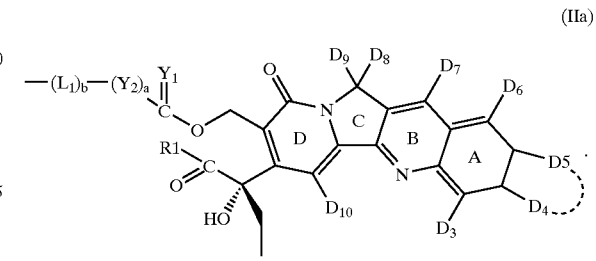

(IIa)

6. A compound of claim 5, of the formula:

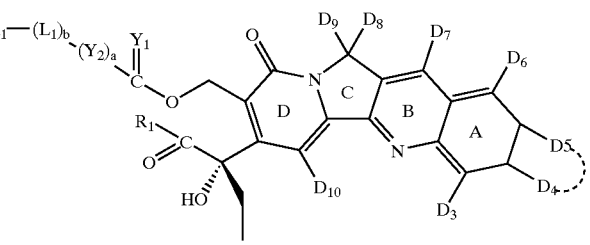

(IIIa)

7. The compound of claim 1, wherein A$_2$ is a polymer residue.

8. The compound of claim 7, wherein said polymer residue further includes a capping group J, selected from the group consisting of OH, NH$_2$, SH, CO$_2$H, C$_{1-6}$ alkyl moieties and

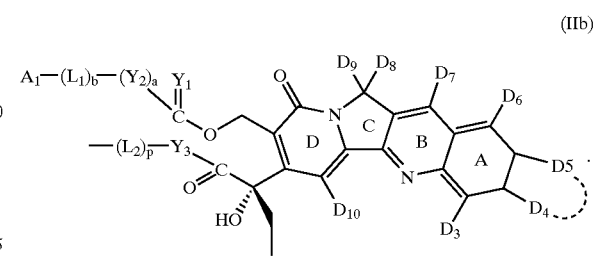

(IIb)

9. A compound of claim 8, of the formula:

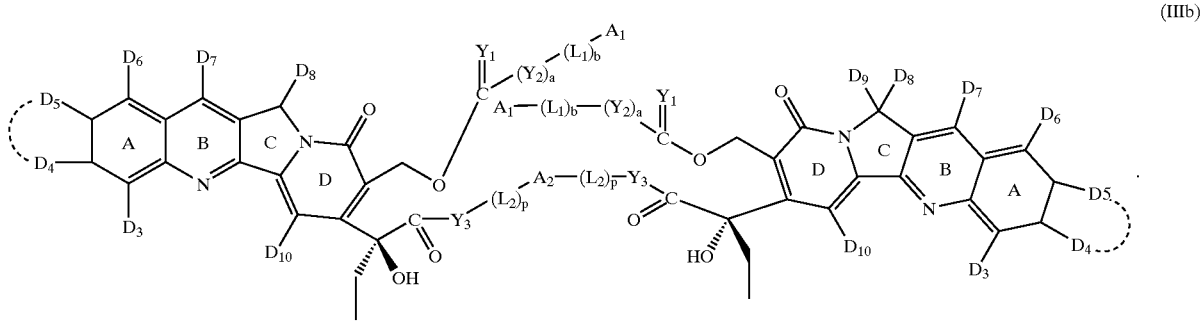

(IIIb)

10. The compound of claim 1, wherein $A_1$ comprises a polyalkylene oxide residue.

11. The compound of claim 1, wherein $A_2$ comprises a polyalkylene oxide residue.

12. The compound of claim 1, wherein $A_1$ comprises a polyethylene glycol residue.

13. The compound of claim 1, wherein $A_2$ comprises a polyethylene glycol residue.

14. The compound of claim 6, wherein $A_1$ comprises a polyethylene glycol residue.

15. The compound of claim 9, wherein $A_2$ comprises a polyethylene glycol residue.

16. The compound of claim 12, wherein $A_1$ is selected from the group consisting
of J—O—$(CH_2CH_2O)_x$—,
J—O—$(CH_2CH_2O)_x$—$CH_2C(O)$—O—,
J—O—$(CH_2CH_2O)_x$—$CH_2CH_2$ $NR_{20}$—,
J—O—$(CH_2CH_2O)_x$—$CH_2CH_2SH$—,
—O—$C(O)CH_2$—O—$(CH_2CH_2O)_x$—$CH_2C(O)$—O—,
—$NR_{20}CH_2CH_2$—O—$(CH_2CH_2O)_x$—$CH_2CH_2NR_{20}$—, and
—$SHCH_2CH_2$—O—$(CH_2CH_2O)_x$—$CH_2CH_2SH$—,
wherein:
x is the degree of polymerization;
$R_{20}$ is selected from the group consisting of hydrogen, $C_{1-6}$ alkyls, $C_{1-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy and
J is a capping group.

17. The compound of claim 13, wherein $A_2$ is selected from the group consisting
of J—O—$(CH_2CH_2O)_x$—,
J—O—$(CH_2CH_2O)_x$—$CH_2C(O)$—O—,
J—O—$(CH_2CH_2O)_x$—$CH_2CH_2NR_{21}$—,
J—O—$(CH_2CH_2O)_x$—$CH_2CH_2SH$—,
—O—$C(O)CH_2$—O—$(CH_2CH_2O)_x$—$CH_2C(O)$—O—,
—$NR_{21}CH_2CH_2$—O—$(CH_2CH_2O)_x$—$CH_2CH_2NR_{21}$—, and
—$SHCH_2CH_2$—O—$(CH_2CH_2O)_x$—$CH_2CH_2SH$—,
herein:
x is the degree of polymerization;
$R_{21}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cyloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy and
J is a capping group.

18. The compound of claim 16, wherein $A_1$ comprises —O—$(CH_2CH_2O)_x$— and x is a positive integer selected so that the weight average molecular weight is at least about 20,000 Da.

19. The compound of claim 17, wherein $A_2$ comprises —O—$(CH_2CH_{20})_x$— and x is a positive integer selected so that the weight average molecular weight thereof is at least about 20,000 Da.

20. The compound of claim 16, wherein $A_1$ has a weight average molecular weight of from about 20,000 Da to about 100,000 Da.

21. The compound of claim 17, wherein $A_2$ has a weight average molecular weight of from about 20,000 Da to about 100,000 Da.

22. The compound of claim 16, wherein $A_1$ has a weight average molecular weight of from about 25,000 Da to about 60,000 Da.

23. The compound of claim 17, wherein $A_2$ has a weight average molecular weight of from about 25,000 Da to about 60,000 Da.

24. The compound of claim 1, wherein $L_1$ is selected from the group consisting of:
$(CH_2)_n$,
$(CH_2)_3NH$—$C(O)$
$(CH_2)_3NH$—
—$NH(CH_2CH_2O)_n(CH_2)_nNR_{22}$—,
—$NH(CH_2CH_2O)_n$—,
—$NH(C_{23}R_{24})_nO$—,
—$C(O)(CR_{23}R_{24})_nNHC(O)(CR_{25}R_{26})_qNR_{27}$—,
—$C(O)O(CH_2)_nO$—,
—$C(O)(CR_{23}R_{24})_nNR_{27}$—,
—$C(O)NH(CH_2CH_2O)_n(CH_2)_nNR_{27}$—,
—$C(O)O$—$(CH_2CH_2O)_nNR_{27}$—,
—$C(O)NH(CR_{23}R_{24})_nO$—,
—$C(O)O(CR_{23}R_{24})_nO$—,
—$C(O)NH(CH_2CH_2O)_n$—,

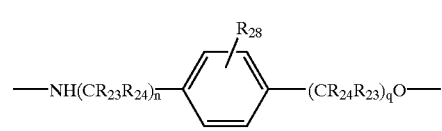

and

-continued

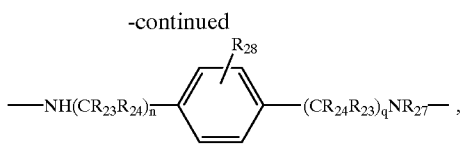

wherein $R_{22-27}$ are independently selected from the group consisting of hydrogen, $C_{1-6}$ alkyls, $C_{3-12}$ branched alkyls, $C_{3-8}$ cycloalkyls, $C_{3-8}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{28}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and n and q are independently selected positive integers.

25. The compound of claim 1, wherein $L_2$ is selected from the group consisting of:

$(CH_2)_j$
$(CH_2CH_2O)_2(CH_2)_2NH$,
—$NH(CH_2CH_2O)_j(CH_2)_kNR_{29}$—,
—$NH(CH_2CH_2O)_j$—,
—$NH(CR_{30}R_{31})_jO$—,
—$C(O)(CR_{30}R_{31})_jNHC(O)(CR_{32}R_{33})_jNR_{29}$—,
—$C(O)O(CH_2)_kO$—,
—$C(O)(CR_{30}R_{31})_jNR_{29}$—,
—$C(O)NH(CH_2CH_2O)_j(CH_2)_kNR_{29}$—,
—$C(O)O$—$(CH_2CH_2O)_jNR_{29}$—,
—$C(O)NH(CR_{30}R_{31})_jO$—,
—$C(O)O(CR_{30}R_{31})_jO$—,
—$C(O)NH(CH_2CH_2O)_j$—,

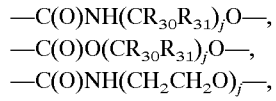

and

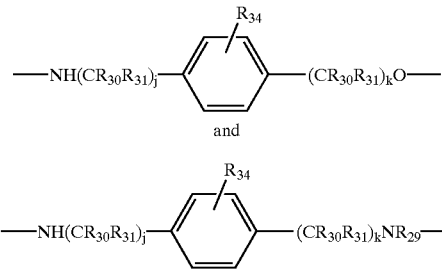

wherein $R_{29-33}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_{34}$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy, $NO_2$, haloalkyl and halogen; and j and k are independently selected positive integers.

26. A compound of claim 1, selected from the group consisting of

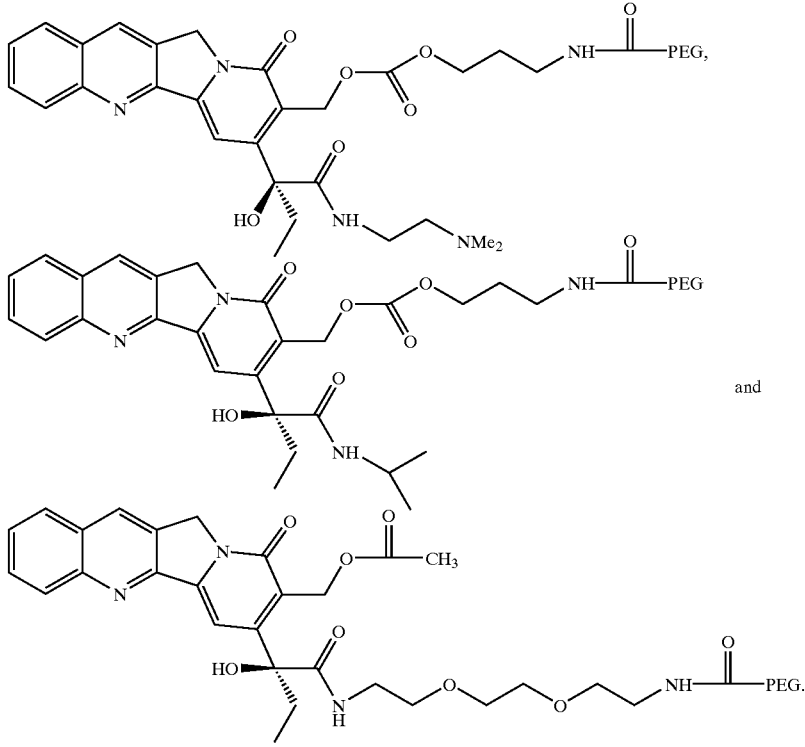

27. A compound of claim 1, selected from the group consisting of

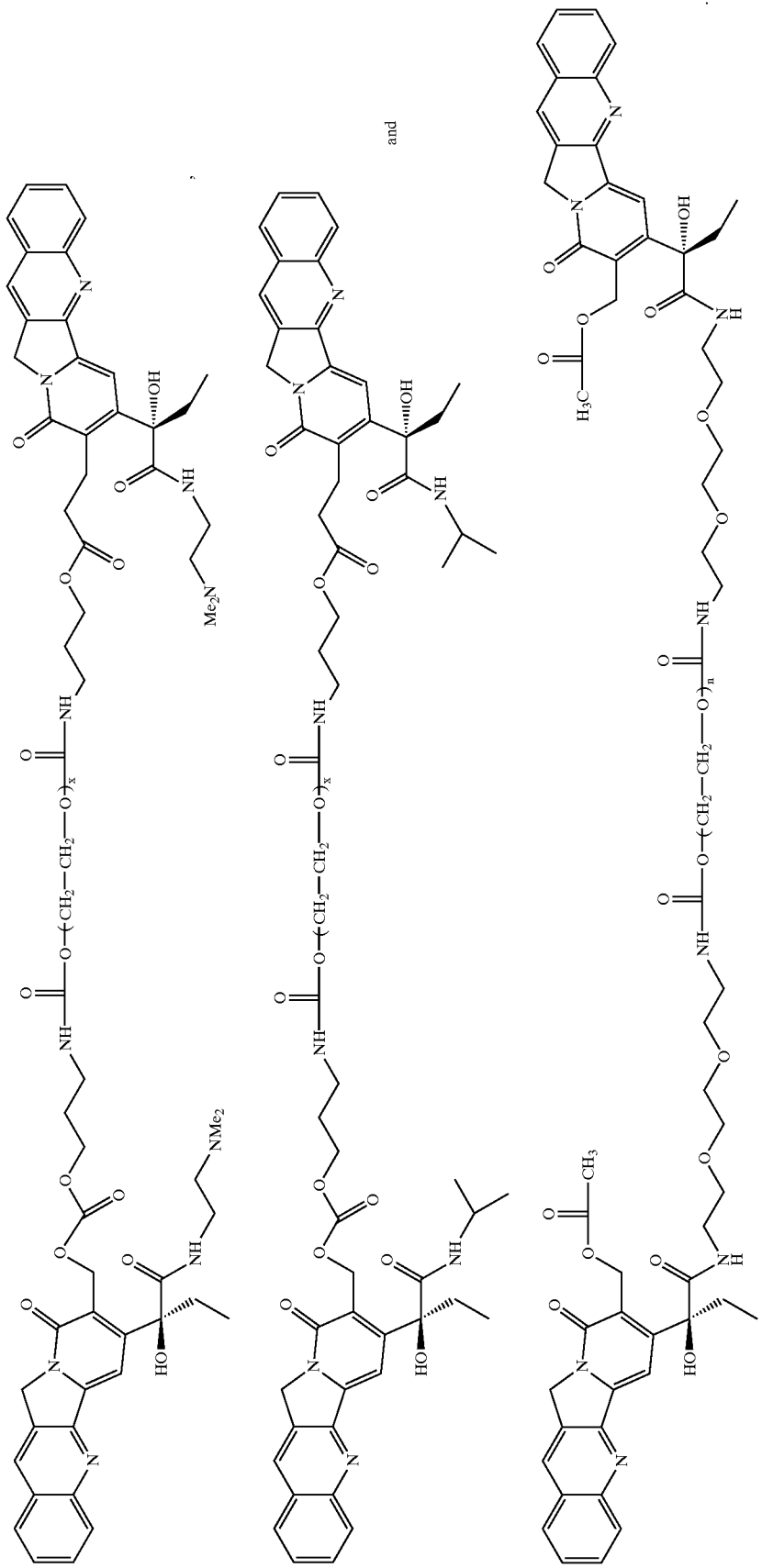

28. A method of preparing a camptothecin analog, comprising:

a) reacting a camptothecin derivative of the formula:

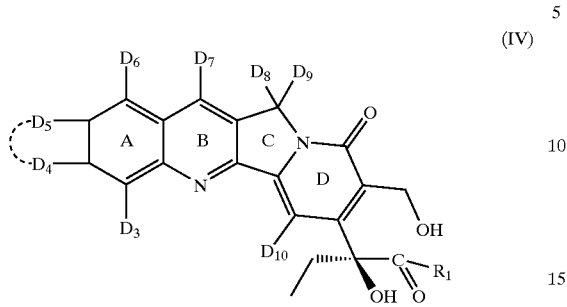

(IV)

wherein:

$R_1$ is selected from the group consisting of amino acid residues, peptide residues containing form about 2 to about 10 amino acids, $Y_3$—$(L_2)_p$—$A_2$ and $R_2$;

$Y_3$ is O, S or $NR_3$;

p is zero or one;

$L_2$ is a bifunctional linker;

$A_2$ is selected from the group consisting of hydrogen, amino protecting groups, $NR_8R_9$, amino acid residues, peptide residues containing from about 2 to about 10 amino acids, polymeric residues, $R_{10}$, $SR_{11}$, $NC(O)R_{12}$;

$D_3$–$D_7$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls, $C_{1-8}$ alkoxys, $C_{1-8}$ hydroxy-alkyls, $C_{1-8}$ aminoalkoxy, aryloxys, gycals, $CO_2R_{13}$, $R_{14}$, nitro, cyano, halo, hydroxyl, amino, $SR_{15}$, $NR_{16}R_{17}$ or $OR_{18}$, where $D_4$ and D5 optionally, when taken together, form a saturated 3–7 membered heterocyclic ring which may contain O, S or $NR_{19}$ groups, where $R_{19}$ is hydrogen or a $C_{1-6}$ alkyl;

$D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls and $C_{1-8}$ hydroxyalkyls; $D_{10}$ is H, and $R_{2-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

with a blocked bifunctional spacer to form a protected intermediate, and b) deprotecting said protected intermediate and reacting the resultant deprotected intermediate with an activated polymer under conditions sufficient to cause a polymeric conjugate to be formed.

29. A method of preparing a polymer conjugate, comprising a) reacting a compound of the formula

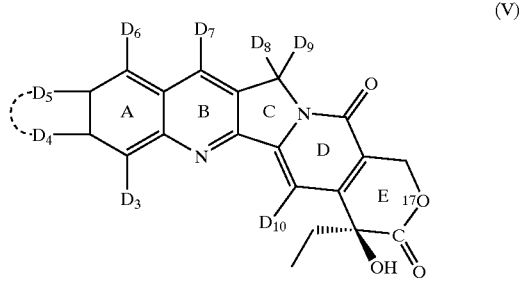

(V)

wherein:

$D_3$–$D_7$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls, $C_{1-8}$ alkoxys, $C_{1-8}$ hydroxy-alkyls, $C_{1-8}$ aminoalkoxy, aryloxys, gycals, $CO_2R_{13}$, $R_{14}$, nitro, cyano, halo, hydroxyl amino, $SR_{15}$, $NR_{16}R_{17}$ or $OR_{18}$, where $D_4$ and $D_5$ optionally, when taken together, form a saturated 3–7 membered heterocyclic ring which may contain O, S or $NR_{19}$ groups, where $R_{19}$ is hydrogen or a $C_{1-6}$ alkyl;

$D_8$–$D_9$ are independently selected from the group consisting of H, $C_{1-8}$ straight or branched alkyls, substituted $C_{1-8}$ straight or branched alkyls, aryls, substituted aryls, arylalkyls, substituted aryalkyls, $C_{1-8}$ alkylaryls and $C_{1-8}$ hydroxyalkyls; $D_{10}$ is H, and $R_{8-18}$ are independently selected from the group consisting of hydrogen, $C_{1-6}$ alkyls, $C_{3-19}$ branched alkyls, $C_{3-8}$ cycloalkyls, $C_{1-6}$ substituted alkyls, $C_{1-6}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

with a blocked bifunctional spacer in an inert solvent under conditions sufficient to open the E lactone and form a protected intermediate of formula (VI)

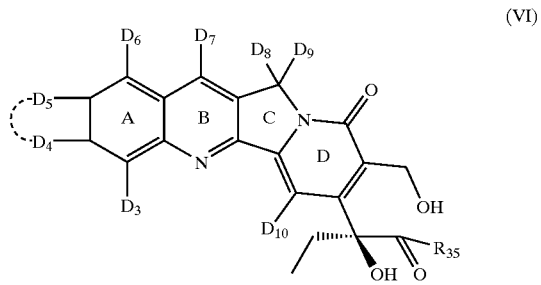

(VI)

wherein $R_{35}$ is a residue of a blocked bifunctional spacer;

b) acylating the $C_{17}$ OH of said blocked intermediate; and c) deblocking said blocked intermediate and reacting at least about 2 equivalents of the resultant deblocked intermediate with an activated polymer under conditions sufficient to cause a polymeric conjugate to be formed.

30. A method of treating a topoisomerase I inhibitor-related disease in mammals, comprising administering an effective amount of a compound of claim 1 to a mammal in need of such treatment.

* * * * *

UNITED STATES PATENT AND TRADEMARK OFFICE
CERTIFICATE OF CORRECTION

PATENT NO. : 6,608,076 B1
DATED : August 19, 2003
INVENTOR(S) : Greenwald et al.

It is certified that error appears in the above-identified patent and that said Letters Patent is hereby corrected as shown below:

Column 23,
Line 18, "$N_3$" should read -- $NR_3$ --;
Lin2 21, "$NR_7$" should read -- $NR_4$ --;
Line 53, "gyrals" should read -- gycals --;
Line 54, "$NR_{16}SR_{17}$" should read -- $NR_{16}R_{17}$ --;

Column 24,
Lines 30-46, formula (IIIa) should appear as follows:

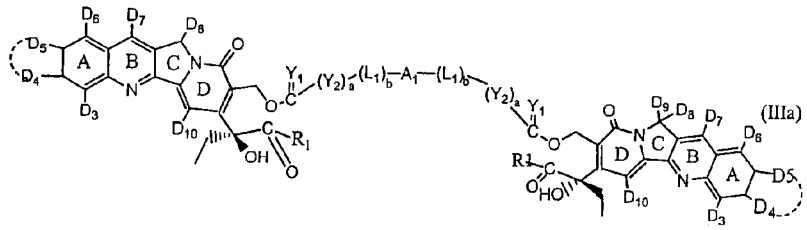

Column 25,
Line 45, "$C_{1-12}$ branched alkyls" should read -- $C_{3-12}$ branched alkyls --;
Line 61, "herein" should read -- wherein --;

Column 26,
Line 26, "-O-$(CH_2CH_{20})_x$-" should read -- -O-$(CH_2CH_2O)_x$- --;

Column 27,
Line 11, the second instance of "$C_{3-8}$" should read -- $C_{1-6}$ --;

Column 31,
Line 21, "form" should read -- from --;
Line 41, "D5" should read -- $D_5$ --;

UNITED STATES PATENT AND TRADEMARK OFFICE
CERTIFICATE OF CORRECTION

PATENT NO.    : 6,608,076 B1
DATED         : August 19, 2003
INVENTOR(S)   : Greenwald et al.

It is certified that error appears in the above-identified patent and that said Letters Patent is hereby corrected as shown below:

Column 32,
Line 34, the second instance of "$C_{1-6}$" should read -- $C_{3-8}$ --.

Signed and Sealed this

Fifth Day of October, 2004

JON W. DUDAS
*Director of the United States Patent and Trademark Office*